(12) United States Patent
Kodama et al.

(10) Patent No.: US 10,772,887 B2
(45) Date of Patent: Sep. 15, 2020

(54) ANTI-HTLV-1 DRUG AND THERAPEUTIC AGENT FOR HTLV-1-ASSOCIATED MYELOPATHY/TROPICAL SPASTIC PARAPARESIS (HAM/TSP)

(71) Applicant: Kagoshima University, Kagoshima-shi, Kagoshima (JP)

(72) Inventors: Daisuke Kodama, Kogoshima (JP); Shuji Izumo, Kagoshima (JP)

(73) Assignee: Kagoshima University, Kagoshima (JP)

(*) Notice: Subject to any disclaimer, the term of this patent is extended or adjusted under 35 U.S.C. 154(b) by 0 days.

(21) Appl. No.: 16/322,356

(22) PCT Filed: Aug. 2, 2017

(86) PCT No.: PCT/JP2017/028094
§ 371 (c)(1),
(2) Date: Jan. 31, 2019

(87) PCT Pub. No.: WO2018/025923
PCT Pub. Date: Feb. 8, 2018

(65) Prior Publication Data
US 2019/0160067 A1 May 30, 2019

(30) Foreign Application Priority Data
Aug. 3, 2016 (JP) .................. 2016-152871

(51) Int. Cl.
*A61K 31/506* (2006.01)
*A61P 25/00* (2006.01)
*A61K 45/00* (2006.01)
*A61P 19/00* (2006.01)

(52) U.S. Cl.
CPC ............ *A61K 31/506* (2013.01); *A61K 45/00* (2013.01); *A61P 19/00* (2018.01); *A61P 25/00* (2018.01)

(58) Field of Classification Search
CPC ......... A61K 31/506; A61P 19/00; A61P 25/00
See application file for complete search history.

(56) References Cited

U.S. PATENT DOCUMENTS

2006/0234931 A1* 10/2006 Biggs, III ............ G01N 33/573
                                                            514/7.5
2007/0149508 A1* 6/2007 Noronha .............. C07D 417/06
                                                            514/218

FOREIGN PATENT DOCUMENTS

JP     2013-119531 A     6/2013

OTHER PUBLICATIONS

Karal-Yilmaz et al., J. Mater Sci: Mater Med vol. 24, pp. 147-153. Published 2013 (Year: 2013).*
Best et al., (Clinical and Experimental Immunology vol. 146 pp. 226-233. Published 2006) (Year: 2006).*
Pinto et al., (Brazilian Journal of Infectious Diseases vol. 19 pp. 578-584. Published 2015. Entry A7 in IDS of Jan. 31, 2019 (Year: 2015).*
Pillat (Central Nervous System Agents in Medicinal Chemistry vol. 11 pp. 1-7. Published 2011) (Year: 2011).*
Best (British Society for Immunology, Clinical and Experimental Immunology vol. 146 pp. 226-233. Published 2006). (Year: 2006).*
Pinto (The Brazilian Journal of Infectious Diseases vol. 19 pp. 578-584. Published 2015). (Year: 2015).*
International Search Report dated Oct. 3, 2017, in PCT/JP2017/028094.
Dumais et al., "T-Cell Receptor/CD28 Engagement When Combined with Prostaglandin E2 Treatment Leads to Potential Activation of Human T-Cell Leukemia Virus Type 1," Journal of Virology, Oct. 2003, 77(20):11170-11179.
Iwasaki et al., "Infiltration of Helper/Inducer T Lymphocytes Heralds Central Nervous System Damage in Human T-cell Leukemia Virus Infection," American Journal of Pathology, May 1992, 140(5):1003-1008.
Lee et al., "Lck is a key target of imatinib and dasatinib in T-cell activation," Leukemia, 2010, 24(4):896-900 and supplemental pages.
Nose et al., "Ex Vivo Analysis of Human T Lymphotropic Virus Type 1-Specific CD4+ Cells by Use of a Major Histocompatibility Complex Class II Tetramer Composed of a Neurological Disease-Susceptibility Allele and Its Immunodominant Peptide," J. Infect. Dis., Dec. 15, 2007, 196(12):1761-1772.
Pinto et al., "T cell receptor signaling pathway is overexpressed in CD4+ T cells from HAM/TSP individuals," The Brazilian Journal of Infectious Diseases, 2015, 19(6):578-584.
Samraj et al., "The tyrosine kinase Lck is a positive regulator of the mitochondrial apoptosis pathway by controlling Bak expression," Oncogene, 2006, 25(2):186-197.
Stephen et al. "Subcellular distribution of Lck during CD4 T-cell maturation in the thymic medulla regulates the T-cell activation threshold," PNAS, May 8, 2012, 109(19):7415-7420.

* cited by examiner

*Primary Examiner* — Timothy P Thomas
*Assistant Examiner* — George W Kosturko
(74) *Attorney, Agent, or Firm* — Foley & Lardner LLP

(57) ABSTRACT

A novel therapeutic agent and novel anti-HTLV-1 drug for HTLV-1-associated myelopathy/tropical spastic paraparesis (HAM/TSP) is provided. A substance capable of inhibiting tyrosine kinase encoded by the ABL1 gene is contained as an active ingredient.

2 Claims, 32 Drawing Sheets

Fig. 6

| Gene symbol | Product | Accession number | Gene ID | Gene location | Relative expression (fold change ± 2SD) | Function and localization |
|---|---|---|---|---|---|---|
| MUC3A | mucin 3A, cell-surface associated | AF007192 | 4584 | 7q22 | 40.60±35.8 | Unknown; O-glycosylation in S/T/P repeat |
| NAF1 | nuclear assembly factor 1 homolog (S. cerevisiae) | NM_138386 | 92345 | 4q32.2 | 13.70±4.92 | RNA binding, protein binding |
| ZC3H12D | Zinc finger CCCH-type containing 12D | NM_207360 | 340152 | 6q25.1 | 11.34±7.00 | Endonuclease activity; regulates MΦ |
| POFUT2 | Protein O-fucosyltransferase 2 isoform A | NM_015227 | 23275 | 21q22.3 | 10.71±3.10 | O-glycosylation in S/T residues in EGF or thrombospondin motifs |
| C14orf72 | Chromosome 14 open reading frame | XM_096733 | 145200 | 14q32.31 | 9.73±4.40 | hypothetical |
| CKS2 | CDC28 protein kinase regulatory subunit 2 | NM_001827 | 1164 | 9q22 | 9.13±5.22 | Cell cycle, cell proliferation, spindle organization |
| SMC4 | Structural maintenance of chromosome 4 | NM_005496 | 10051 | 3q26.1 | 7.38±5.02 | ATP, nucleotide, protein binding, cell cycle, division |
| SOX21 | SRY (sex determining region Y)-box 21 | NM_007084 | 11166 | 13q31-q32 | 6.83±3.38 | transcription factor activity |
| KLHL21 | kelch-like protein 21 (Drosophila) | NM_014851 | 9903 | 1p36.31 | 6.81±5.44 | Protein binding |
| RABGAP1L | RAB GTPase activating protein 1-like isoform A | NM_014857 | 9910 | 1q24 | 6.71±4.32 | GTPase activator activity; intracellular |
| ATP1B1 | Na+/K+-ATPase beta 1 subunit isoform a | NM_001677 | 481 | 1q24 | 6.68±3.1 | K ion binding; plasma membrane protein |
| WDR41 | WD repeat domain 41 | NM_018268 | 55255 | 5q13.3 | 6.49±3.82 | unknown |
| TDP1 | tyrosyl-DNA phosphodiesterase 1 | NM_018319 | 55775 | 14q32.11 | 6.39±4.20 | DNA repair, binding |
| BCL2L13 | BCL2-like protein 13 (apoptosis facilitator) | NM_015367 | 23786 | 22q11.1 | 6.30±4.14 | Caspase activator activity |
| RPS6KA5 | ribosomal protein S6 kinase, 90kDa, polypeptide 5 | NM_004755 | 9252 | 14q31-q32.1 | 6.27±3.88 | ATP binding; cytoplasm, nucleus |
| MAML1 | Mastermind-like [domain containing] 1 | NM_005491 | 9794 | 5q35 | 5.95±0.62 | Regulation of transcription; nucleus |
| RABEP1 | rabaptin, RAB GTPase binding effector protein 1 isoform 1 | NM_004703 | 9135 | 17p13.2 | 5.54±2.42 | membrane fusion, GTPase activator activity; cytoplasm, endosome |
| IL-6ST | IL-6 signal transducer isoform 1 precursor (gp130, oncostatin M receptor) | NM_002184 | 3572 | 5q11 | 5.32±2.30 | IL-6, -11, -27 receptor activity; positive regulation of T cell proliferation; plasma membrane |
| TMEM39A | Transmembrane protein 9A | NM_018266 | 55254 | 3q13.33 | 5.20±1.88 | plasma membrane; transmembrane protein |
| S100P | S100 calcium binding protein P | NM_005980 | 6286 | 4p16 | 5.06±3.24 | Calcium and magnesium ion binding; cytoplasm, nucleus |
| AFF4 | AFF/FMR2 family, member 4 | NM_014423 | 27125 | 5q31 | 4.86±4.94 | Regulation of transcription; nucleus |
| SLFN5 | schlafen family, member 5 | NM_144975 | 162394 | 17q12 | 4.83±1.06 | ATP, nucleotide binding; cell differentiation; nucleus |
| SOD2 | Superoxide dismutase 2, mitochondrial | BC016934 | 6648 | 6q25.3 | 4.83±1.92 | Magnesium ion binding; nucleus |
| RILPL2 | Rab interacting lysosomal protein-like 2 | NM_145058 | 196383 | 12q24.31 | 4.76±3.08 | Identical protein binding; cytoplasm, cytosol |
| PMFBP1 | Polyamine modulated factor 1 (PMF-1) binding protein 1 | NM_031293 | 83449 | 16q22.2 | 4.63±1.72 | Unknown; cytoplasm |
| RAN | Ras related nuclear protein | NM_006325 | 5901 | 12q24.3 | 4.50±0.98 | GTP binding, GTPase activity, mitotic spindle organization; cytosol, nucleus |
| PWP1 | PWP1 homolog (S. cerevisiae) | CR621244 | 11137 | 12q23.3 | 4.32±3.90 | Transcription; nucleus |
| MED28 | Mediator complex subunit 28 | NM_025205 | 80306 | 4p16 | 4.29±1.58 | actin binding, protein binding, regulation of transcription; cytoplasm, membrane, nucleus |

Fig. 7

| Gene symbol | Product | Accession number | Gene ID | Gene location | Relative expression (fold change ± 2SD) | Function and localization |
|---|---|---|---|---|---|---|
| HES2 | HES2 (hairy and enhancer of split 2 (Drosophila)) protein | BC012091 | 54626 | 1p36.31-p36.11 | 4.17±2.78 | DNA binding, transcription regulator activity; nucleus |
| FAM133B | family with sequence similarity 133, member B(hypothetical protein LOC257415) | NM_152789 | 257415 | 7q21.2 | 4.14±1.90 | Unkown |
| RRN3 | RNA polymerase I-specific transcription initiation factor RRN3 (TIF-IA) | NM_018427 | 54700 | 16p12 | 4.06±2.14 | Regulation of transcription; nucleoplasm, nucleus |
| HERPUD1 | homocysteine-inducible, endoplasmic reticulum stress-inducible, ubiquitin-like domain member 1 protein | NM_014685 | 9709 | 16q12.2-q13 | 4.04±2.58 | protein binding, response to unfolded protein; ER |
| PRPS1L1 | phosphoribosyl pyrophosphate synthetase 1-like 1 | NM_175886 | 221823 | 7p21.1 | 3.86±2.14 | ATP, magnesium ion binding, kinase activity; cellular component |
| FBXO3 | F-box protein 3 | NM_012175 | 26273 | 11p13 | 3.81±2.04 | ubiquitin-protein ligase activity, proteolysis |
| PDCD2 | programmed cell death 2 isoform 1 | NM_002598 | 5134 | 6q27 | 3.75±1.98 | DNA, protein, zinc ion binding, apoptosis; cytoplasm, nucleus |
| SNAPC5 | small nuclear RNA activating complex, polypeptide 5, 19kDa subunit | BC014315 | 10302 | 15q22.31 | 3.75±1.66 | Regulation of transcription; nucleus |
| BIRC3 | baculoviral IAP repeat-containing 3 (cIAP-2) | NM_001165 | 330 | 11q22 | 3.74±1.90 | ubiquitin-protein ligase activity, zinc ion binding, anti-apoptosis, signal transduction; cytoplasm, nucleus |
| ELN | elastin | BC065566 | 2006 | 7q11.23 | 3.71±2.26 | extracellular matrix constituent; extracellular matrix |
| KRT1 | keratin 1 | NM_006121 | 3848 | 12q12-q13 | 3.70±1.04 | Protein, sugar binding, receptor activity, cytoskeleton; plasma membrane |
| GALNT11 | UDP-N-acetyl-α-D-galactosamine:polypeptide N-acetylgalactosaminyltransferase 11 (GalNAc-T11) | NM_022087 | 63917 | 7q34-36 | 3.69±1.46 | polypeptide N-acetylgalactosaminyltransferase activity; Golgi |
| IKZF5 | IKAROS family zinc finger protein 5 | NM_022466 | 64376 | 10q26 | 3.65±1.10 | DNA, zinc ion binding; intracellular, nucleus or NOT nucleus |
| TBC1D23 | TBC1 domain family, member 23 | NM_018309 | 55773 | 3q12.1-12.2 | 3.57±2.18 | Rab GTPase activator activity; intracellular |
| MRPL41 | mitochondrial ribosomal protein L41 | NM_032477 | 64975 | 9q34.3 | 3.52±1.56 | structural constituent of ribosome, apoptosis, cell cycle,translation; mitochondria, ribosome |
| NEUROG3 | neurogenin 3 (class A basic helix-loop-helix protein 7) | NM_020999 | 50674 | 10q21.3 | 3.49±2.26 | Nervous system development, positive regulation of transcription from RNA polymerase II promoter; nucleus |
| CIRH1A | cirrhosis, autosomal recessive 1A (cirhin) | NM_032830 | 84916 | 16q22.1 | 3.49±0.48 | Molecular function; nucleolar, nucleus |
| NDUFB3 | NADH dehydrogenase (ubiquinone) 1 beta | NM_002491 | 4709 | 2q31.3 | 3.39±1.18 | NADH dehydrogenase (ubiquinone) activity, mitochondrial electron transport; mitochondria |
| PLA2G4D | phospholipase A2, group IVD (cytosolic) | NM_178034 | 283748 | 15q15.1 | 3.37±1.20 | calcium ion binding, hydrolase activity, phospholipase A2 activity; Cytosol, cytoplasm |
| PTBP1 | polypyrimidine tract binding protein 1 | NM_002819 | 5725 | 15q15.1 | 3.36±1.30 | RNA splicing; nucleolous, nucleoplasm, nucleus |

Fig. 8

| Gene symbol | Product | Accession number | Gene ID | Gene location | Relative expression (fold change ± 2SD) | Function and localization |
|---|---|---|---|---|---|---|
| HAND1 | heart and neural crest derivatives expressed 1, bHLHa27 | NM_004821 | 9421 | 5q33 | 3.34±1.82 | protein heterodimerization activity, transcription ; nucleus |
| GMCL1 | germ cell-less homolog 1 (Drosophila) | NM_178439 | 64395 | 2p13.3 | 3.34±2.76 | protein binding, cell differentiation; nucleus |
| FAT2 | FAT tumor suppressor homolog 2 (Drosophila) | NM_001447 | 2196 | 5q32-33 | 3.29±0.84 | calcium ion, protein binding, cell adhesion; plasma membrane |
| WARS2 | tryptophanyl tRNA synthetase 2, mitochondrial | NM_201263 | 10352 | 1p13.3-13.1 | 3.29±2.74 | ATP, nucleotide binding, tryptophan-tRNA ligase activity, cytoplasm, mitochondria |
| CDX4 | caudal type homeobox transcription factor 4 | NM_005193 | 1046 | Xq13.2 | 3.29±2.02 | Sequence-specific DNA binding, transcription factor; nucleus |
| TDG | thymine-DNA glycosylase | NM_003211 | 6996 | 12q24.1 | 3.27±1.26 | DNA N-glycosylase activity, damaged DNA, mismatched DNA binding; nucleus |
| CCDC85C | coiled-coil domain containing [protein] 85C | BC031990 | 317762 | 14q32.31 | 3.27±1.36 | Unknown |
| ABL1 | c-abl oncogene 1, receptor tyrosine kinase | M14755 | 25 | 9q34.1 | 3.26±2.06 | Apoptosis, cell cycle, cell adhesion, actin cytoskeleton organization, peptidyl-tyrosine phosphorylation, transcription, signal transduction;intracellular |
| PRLH | Prolactin releasing hormone | NM_015893 | 51052 | 2q37.3 | 3.25±1.54 | Hormone activity; cytoplasm, extracellular |
| OASL | 2'-5'-oligoadenylate synthetase-like isoform a | NM_003733 | 8638 | 12q24.2 | 3.24±2.38 | ATP, DNA, double-stranded RNA binding, thyroid hormone receptor binding, transferase activity; cytoplasm, nucleus |
| HCP5 | HLA complex P5 | NM_006674 | 10866 | 6p21.3 | 3.23±1.98 | Defense response; plasma membrane |
| CCT6A | chaperonin containing TCP1, subunit 6A isoform a | NM_001762 | 908 | 7p11.2 | 3.22±1.20 | ATP, nucleotide, unfolded protein binding; cytoplasm |
| SMAD4 | SMAD family member 4 | NM_005359 | 4089 | 18q21.1 | 3.16±0.90 | R-SMAD, collagen binding, BMP signaling; cytosol, cytoplasm, nucleoplasm, nucleus |
| SMN2 | survival of motor neuron 2, centromeric | NM_022877 | 6607 | 5q13 | 3.15±1.02 | RNA, protein binding, RNA, mRNA splicing, cell death; cytosol, nucleus |
| CCL13 | chemokine (C-C motif) ligand 13 | NM_005408 | 6357 | 17q11.2 | 3.14±1.44 | chemokine activity, signal transducer activity, cell-cell signaling, inflammatory response; plasma membrane |
| TRIM23 | tripartite motif-containing 23 (ADP-ribosylation factor domain protein 1 isoform alpha) | NM_001656 | 373 | 5q12.3 | 3.14±0.92 | GDP, GTP, nucleotide binding; Golgi, cytoplasm |
| PFKFB2 | 6-phosphofructo-2-kinase/fructose-2, 6-biphosphatase 2 isoform a | NM_006212 | 5208 | 1q31 | 3.13±1.32 | ATP, nucleotide binding, 6-phophofrukto-2-kinase hydrolase, kinase, transferase activity; cytosol |
| ERN1 | ER to nucleus signalling 1 isoform 2 | NM_152461 | 2081 | 17q24.2 | 3.08±0.74 | Endonuclease activity, cell cycle arrest, mRNA processing, regulation of transcription; ER, nuclear inner membrane |
| GABPB2 | GA binding protein transcription factor, beta subunit 2 isoform beta 1 | NM_005254 | 126626 | 1q21.3 | 3.07±1.86 | protein binding, transcription factor activity; nucleus |
| RAPGEF1 | Rap guanine nucleotide exchange factor (GEF) 1 (guanine nucleotide-releasing factor 2 isoform b) | NM_198679 | 2889 | 9q34.3 | 3.06±2.20 | SH3 domain binding, guanyl-nucleotide exchange factor activity, protein binding; cytosol, endosome, intracellular |

Fig. 9

| Gene symbol | Product | Accession number | Gene ID | Gene location | Relative expression (fold change ± 2SD) | Function and localization |
|---|---|---|---|---|---|---|
| YTHDC1 | YTH domain containing protein 1 | NM_133370 | 91746 | 4q13.2 | 3.04±0.96 | RNA splicing, mRNA processing; nucleus |
| MORF4L1 | mortality factor 4 like 1 | NM_206839 | 10933 | 15q24 | 3.03±1.82 | DNA repair, chromatin modification, histone H2A acetylation, histone H4 acetylation, histone deacetylation; nucleus |
| SOX3 | SRY (sex determining region Y)-box 3 | NM_005634 | 6658 | Xq27.1 | 3.02±1.54 | DNA binding; nucleus |
| SNRPG | small nuclear ribonucleoprotein polypeptide G | NM_003096 | 6637 | 2p13.3 | 2.99±1.46 | RNA binding, RNA splicing, protein binding; cytosol, nucleus |
| POLR2K | DNA directed RNA polymerase II polypeptide K | NM_005034 | 5440 | 8q22.2 | 2.98±1.14 | DNA binding, DNA-directed RNA polymerase activity, zinc ion binding; nucleoplasm, nucleus |
| ZMAT2 | zinc finger, matrin type 2 | NM_144723 | 153527 | 5q31.3 | 2.97±1.46 | DNA binding, zinc ion binding; intracellular, nucleus |
| AATK | apoptosis-associated tyrosine kinase | AK131529 | 9625 | 17q25.3 | 2.95±1.84 | ATP, nucleotide binding, transferase; cytoplasm, mitochondria |
| TSPAN13 | Tetraspanin 13 (TM4SF13, NET-6) | NM_014399 | 27075 | 7q21.1 | 2.90±1.16 | Plasma membrane |
| TAAR5 | trace amine associated receptor 5 (putative neurotransmitter receptor) | NM_003967 | 9038 | 6q23 | 2.88±1.22 | G-protein coupled receptor activity, plasma membrane |
| TMEM126A | transmembrane protein 126A | NM_032273 | 84233 | 11q14.1 | 2.87±0.72 | Molecular function; plasma membrane, mitochondria |
| COMP | cartilage oligomeric matrix protein precursor | NM_000095 | 1311 | 19p13.1 | 2.85±2.16 | calcium ion binding, ECM structure, cell adhesion; extracellular |
| ULBP2 | UL16 binding protein 2 | NM_025217 | 80328 | 6q25 | 2.80±1.52 | MHC class I receptor, NK cell activation; plasma membrane |
| ADAM7 | a disintegrin and metalloproteinase domain | NM_003817 | 8756 | 8q21.2 | 2.76±1.04 | metalloendopeptidase activity, zinc ion binding, proteolysis; plasma membrane |
| HUS1 | HUS1 checkpoint protein | NM_004507 | 3364 | 7p13-12 | 2.75±1.54 | protein binding, protein serine/threonine kinase activity, DNA repair, cell cycle; cytoplasm, nucleus |
| SH3KBP1 | SH3-domain kinase binding protein 1 (Homo sapiens migration-inducing gene 18 protein) | AY423734 | 30011 | Xp22.1-21.3 | 2.74±1.54 | SH3 domain binding, protein binding, apoptosis, cell-cell signaling, endocytosis, focal adhesion; plasma membrane |
| PPM1B | protein phosphatase, Mg2+/Mn2+ dependent, 1B | NM_002706 | 5495 | 2p21 | 2.70±0.74 | hydrolase activity, magnesium ion binding, protein binding, protein serine/threonine phosphatase activity |
| SMURF1 | SMAD specific E3 ubiquitin protein ligase 1 | NM_020429 | 57154 | 7q22.1 | 2.68±1.02 | ubiquitin-protein ligase activity; cytoplasm, plasma membrane |
| SMPX | small muscle protein, X-linked | NM_014332 | 23676 | Xq22.1 | 2.63±0.94 | striated muscle contraction; cytoplasm, nucleus |
| ADAM21 | ADAM metallopeptidase domain 21 preproprotein | NM_003813 | 8747 | 14q24.1 | 2.63±1.08 | zinc ion binding, metalloendopeptidase activity, proteolysis, single fertilization; membrane |
| IGFALS | insulin-like growth factor binding protein, acid labile subunit | NM_004970 | 3483 | 16p13.3 | 2.62±0.68 | IGF binding, protein C-terminus binding, cell adhesion; extracellular region, microsome, soluble fraction |
| NPM1 | nucleophosmin (nucleolar phosphoprotein B23, numatrin) 1 isoform 2 | NM_199185 | 4869 | 5q35 | 2.62±0.60 | NF-kappaB, Tat protein, RNA, histone binding, protein hetero- or homodimerization, anti-apoptosis, cell-aging |
| ZNF407 | zinc finger protein 407 (KIAA1703 protein) | AB051490 | 55628 | 18q23 | 2.61±0.68 | DNA, zinc ion binding, transcription; intracellular, nucleus |

Fig. 10

| Gene symbol | Product | Accession number | Gene ID | Gene location | Relative expression (fold change ± 2SD) | Function and localization |
|---|---|---|---|---|---|---|
| HLA-E | MHC, class I, E precursor | NM_005516 | 3133 | 6p21.3 | 2.61±0.56 | MHC class I receptor activity, antigen processing and presentation; plasma membrane |
| MOBKL3 | Mps One Binder kinase activator-like 3 (yeast) | NM_015387 | 25843 | 2q33.1 | 2.59±1.02 | zinc ion, protein binding; Golgi, cytoplasma, membrane |
| B9D2 | B9 protein domain 2 (hypothetical LOC80776) (preimplantation protein 3 isoform 1) | NM_030578 | 80776 | 19q13.2 | 2.57±0.52 | cell projection organization; cilium, microtubule basal body, nucleus |
| PEX6 | peroxisomal biogenesis factor 6 | NM_000287 | 5190 | 6q21.1 | 2.54±0.94 | ATPase activity, ATP, nucleotide, protein C-terminus binding; cytoplasm, cytosol, peroxisome |
| YWHAZ | tyrosine 3-monooxygenase/tryptophan 5-monooxygenase activation protein, zeta polypeptide | NM_145690 | 7534 | 8q23.1 | 2.52±0.86 | protein domain specific binding, transcription factor binding, anti-apoptosis; cytoplasm, mitochondria, nucleus |
| SUPV3L1 | suppressor of var1, 3-like 1 (S. cerevisiae) | NM_003171 | 6832 | 10q22.1 | 2.49±0.40 | ATP, DNA, RNA, nucleotide binding, DNA helicase activity, hydrolase activity, DNA duplex unwinding; nucleus, mitochondria |
| EIF2S1 | eukaryotic translation initiation factor 2, subunit 1 alpha, 35kDa | NM_004094 | 1965 | 14q23.3 | 2.48±1.22 | RNA, protein binding, translation initiation factor activity; cytoplasm, cytosol, nucleus |
| TUBA1B | tubulin, alpha 1b | AI608782 | 10376 | 12q13.12 | 2.48±0.64 | GTP, protein binding, GTPase activity, microtubule cytoskeleton organization; microtubule |
| HNRPCL1 | heterogeneous nuclear ribonucleoprotein C-like 1 | NM_0010136 | 343069 | 1p36.21 | 2.48±0.60 | RNA binding, nucleotide binding; nucleus |
| POLB | polymerase (DNA directed), beta | NM_002690 | 5423 | 8p11.2 | 2.45±1.12 | DNA-directed DNA polymerase activity, damaged DNA binding, enzyme binding, lyase activity; cytoplasm, nucleoplasm, nucleus, spindle microtubule |
| SRPK3 | SFRS protein kinase 3 | NM_014370 | 26576 | Xq28 | 2.45±0.38 | ATP, nucleotide, protein binding, protein serine/threonine kinase activity, transferase activity; cellular component |
| TSPYL1 | TSPY-like 1 | NM_00309 | 7259 | 6q22-23 | 2.44±0.68 | Molecular function; intracellular, nucleolus, nucleus |
| RAI2 | retinoic acid induced 2 | NM_021785 | 10742 | Xp22 | 2.44±1.18 | Molecular function, , embryonic development; cellular component |
| UQCR11 | ubiquinol-cytochrome c reductase, complex III subunit XI | NM_006830 | 10975 | 19p13.3 | 2.44±0.32 | electron carrier activity, ubiquinol-cytochrome-c reduction activity; mitochondria |
| POLDIP3 | polymerase (DNA-directed), delta interacting protein 3 | NM_032311 | 84271 | 22q13.2 | 2.41±0.44 | RNA binding, nucleotide binding, protein binding; nucleus |
| RPS14 | ribosomal protein S14 | NM_005617 | 6208 | 5q31-33 | 2.38±0.50 | RNA, mRNA 5'-UTR, protein binding, constituent of ribosome, translation regulator activity; cytosol, nuleolous, ribosome |

Fig. 11

| Gene symbol | Product | Accession number | Gene ID | Gene location | Relative expression (fold change ± 2SD) | Function and localization |
|---|---|---|---|---|---|---|
| SMCHD | structural maintenance of chromosomes flexible hinge domain containing 1 | AK126324 | 23347 | 18p11.32 | 2.36±0.46 | ATP, protein binding; chromosome |
| HBS1L | HBS1-like (S. cerevisiae) | AJ459827 | 10767 | 6q23-24 | 2.32±0.42 | GTP, nucletide binding, GTPase activity,translation elongation factor activity |
| SLC4A3 | solute carrier family 4, anion exchanger, member 3 | U05597 | 6508 | 2q36 | 2.22±0.60 | anion transmembrane transporter activity; inorganic anion exchanger activity; transporter activity; plasma membrane |

Fig. 13

| Pathway ID of TRANSPATH database | Molecular name | Pathway name | #Hits in group | Group size | #Hits expected | P-value |
|---|---|---|---|---|---|---|
| CH000003804 | ABL-1a, ABL-1b | Abl ---> TOPBP1 | 2 | 3 | 1 | 0.000213782 |
| CH000000870 | ABL-1a, ABL-1b | Abl ---> Rad52 | 2 | 4 | 1 | 0.000425383 |
| CH000000972 | ABL-1a, ABL-1b | Abl --\| Bcl-xL | 2 | 4 | 1 | 0.000425383 |
| CH000003546 | ABL-1a, ABL-1b | Abl ---> Caspase-9 | 2 | 4 | 1 | 0.000425383 |
| CH000000867 | ABL-1a, ABL-1b | Abl ---> p73α | 2 | 5 | 1 | 0.000705355 |
| CH000000908 | ABL-1a, ABL-1b | Caspase-8 ---> Abl | 2 | 6 | 1 | 0.00105264 |
| CH000000997 | ABL-1a, ABL-1b | Ubc9 --\| p73α | 2 | 7 | 1 | 0.00146618 |
| CH000000895 | ABL-1a, ABL-1b | Fas ---> Abl | 2 | 10 | 1 | 0.00309403 |
| CH000000977 | ABL-1a, ABL-1b | Abl ---> p53 | 2 | 11 | 1 | 0.00376233 |
| CH000000869 | ABL-1a, ABL-1b | p73 pathway | 2 | 24 | 1 | 0.0176695 |
| CH000000711 | SMAD4, Ran, Smurf-1 | TGFβ pathway | 3 | 76 | 1 | 0.0260633 |
| CH000000879 | ABL-1a, ABL-1b, cIAP-2 | Caspase network | 3 | 93 | 1 | 0.0439147 |

ANTI-HTLV-1 DRUG AND THERAPEUTIC AGENT FOR HTLV-1-ASSOCIATED MYELOPATHY/TROPICAL SPASTIC PARAPARESIS (HAM/TSP)

CROSS-REFERENCE TO RELATED APPLICATIONS

This application is the U.S. National Stage of PCT/JP2017/028094 filed Aug. 2, 2017, which claims priority to JP 2016-152871, filed Aug. 3, 2016.

TECHNICAL FIELD

The present invention relates to an anti-HTLV-1 drug for reducing the load of human T lymphotropic virus type 1 and a therapeutic agent for HTLV-1-associated myelopathy that is a disease caused by the human T lymphotropic virus.

BACKGROUND ART

Human T lymphotropic virus type 1 (hereinafter referred to as "HTLV-1") is a retrovirus that is integrated into the genomic DNA of CD4-positive T lymphocytes and infectiously propagated in vive and between individuals. Tumorigenesis of HTLV-1-infected cells causes adult T cell leukemia (ATL), and HTLV-1-infected cells infiltrate into the spinal cord, thereby inducing HTLV-1-associated myelopathy (HAM/TSP: HTLV-1-associated myelopathy/tropical spastic paraparesis, hereinafter also referred to as "HAM") which causes spastic spinal paralysis and dysuria. Further, infiltration of HTLV-1-infected cells into the eye may cause HTLV-1-associated uveitis (HU).

The pathogenic mechanism of HAM among various diseases caused by HTLV-1 described above is unknown except that HTLV-1-infected cells infiltrate into the spinal cord and trigger inflammation. At present, no curative therapy has been established for HAM, and treatment for suppressing inflammation is performed depending on the rate of disease progression and the intensity of inflammation. In a case in which the inflammation is severe, symptoms are likely to progress. In such case, treatment such as steroid therapy or interferon-alpha injection therapy is selected to suppress inflammation and prevent the spinal cord from being destroyed. Specifically, it has been confirmed that oral administration of a corticosteroid (predonisolone) as an anti-inflammatory agent causes the proviral load to decrease to some extent, which is an effect of improving symptoms. However, in many cases, the above treatment cannot achieve complete cure, and there are problems such as a rebound phenomenon due to discontinuation of drugs. The treatment method is further problematic due to side effects such as steroid diabetes, osteoporosis, and immunosuppression.

As described above, there has been a need for therapeutic agents capable of achieving complete cure of HAM caused by HTLV-1. For example, Patent Literature 1 discloses a therapeutic agent for HTLV-1-associated myelopathy including an anti-human CXCL10 antibody that specifically binds to human CXCL10 or a fragment of the antibody.

CITATION LIST

Patent Literature

Patent Literature: JP Patent Publication (Kokai) No. 2013-119531 A

SUMMARY OF INVENTION

Technical Problem

In view of the above circumstances, an object of the present invention is to elucidate signal transduction in peripheral CD4+ T cells as the primary infection lesion in HTLV-1-associated myelopathy patients so as to provide a novel therapeutic agent for HTLV-1-associated myelopathy based on the obtained findings. Another object of the present invention is to provide an anti-HTLV-1 drug for reducing HTLV-1 that causes HTLV-1-associated myelopathy.

Solution to Problem

In order to achieve the above objects, the present inventors conducted intensive studies. Accordingly, the inventors found that it is possible to identify tyrosine kinase ABL involved in the pathway that is specifically expressed in CD4+ T cells from HTLV-1-associated myelopathy patients by conducting pathway analysis or the like using CD4+ T cells from HTLV-1-associated myelopathy patients, thereby allowing ABL1 inhibitors to kill CD4+ T cells from HTLV-1-associated myelopathy patients in a specific manner. The inventors further found that ABL1 inhibitors can also kill CD4+ T cells from an asymptomatic carrier (AC) in a specific manner and can be used as antiviral drugs capable of reducing the viral load in an asymptomatic carrier or the like. The present inventors have completed the present invention based on the above novel findings.

The present invention encompasses the following.
(1) A therapeutic agent for HTLV-1-associated myelopathy/tropical spastic paraparesis (HAM/TSP), which comprises a substance that inhibits a tyrosine kinase encoded by the ABL1 gene as an active ingredient.
(2) The therapeutic agent for HTLV-1-associated myelopathy/tropical spastic paraparesis (HAM/TSP) according to (1), wherein the substance is at least one substance selected from the group consisting of imatinib, nilotinib, and dasatinib.
(3) An anti-HTLV-1 drug, which comprises a substance that inhibits a tyrosine kinase encoded by the ABL gene as an active ingredient.
(4) The anti-HTLV-1 drug according to (3), wherein the substance is at least one substance selected from the group consisting of imatinib, nilotinib, and dasatinib.

The present description includes part or all of the contents as disclosed in the description and/or drawings of Japanese Patent Application No. 2016-152871, which is a priority document of the present application.

Advantageous Effects of Invention

According to the present invention, it is possible to provide a therapeutic agent effective for HTLV-1-associated myelopathy for which no effective therapeutic agents have been conventionally available.

According to the present invention, it is also possible to provide an anti-HTLV-1 drug for reducing HTLV-1 that causes HTLV-1-associated myelopathy.

BRIEF DESCRIPTION OF DRAWINGS

FIG. 6 is a characteristic chart listing genes identified as HAM pathology-specific responsible genes that are overexpressed only in HAM.

FIG. 7 is a characteristic chart listing genes identified as HAM pathology-specific responsible genes that are overexpressed only in HAM.

FIG. 8 is a characteristic chart listing genes identified as HAM pathology-specific responsible genes that are overexpressed only in HAM.

FIG. 9 is a characteristic chart listing genes identified as HAM pathology-specific responsible genes that are overexpressed only in HAM.

FIG. 10 is a characteristic chart listing genes identified as HAM pathology-specific responsible genes that are overexpressed only in HAM.

FIG. 11 is a characteristic chart listing genes identified as HAM pathology-specific responsible genes that are overexpressed only in HAM.

FIG. 13 is a characteristic chart listing HAM pathology-specific pathways identified in Experimental Example 1.

DESCRIPTION OF EMBODIMENTS

Figure 1:
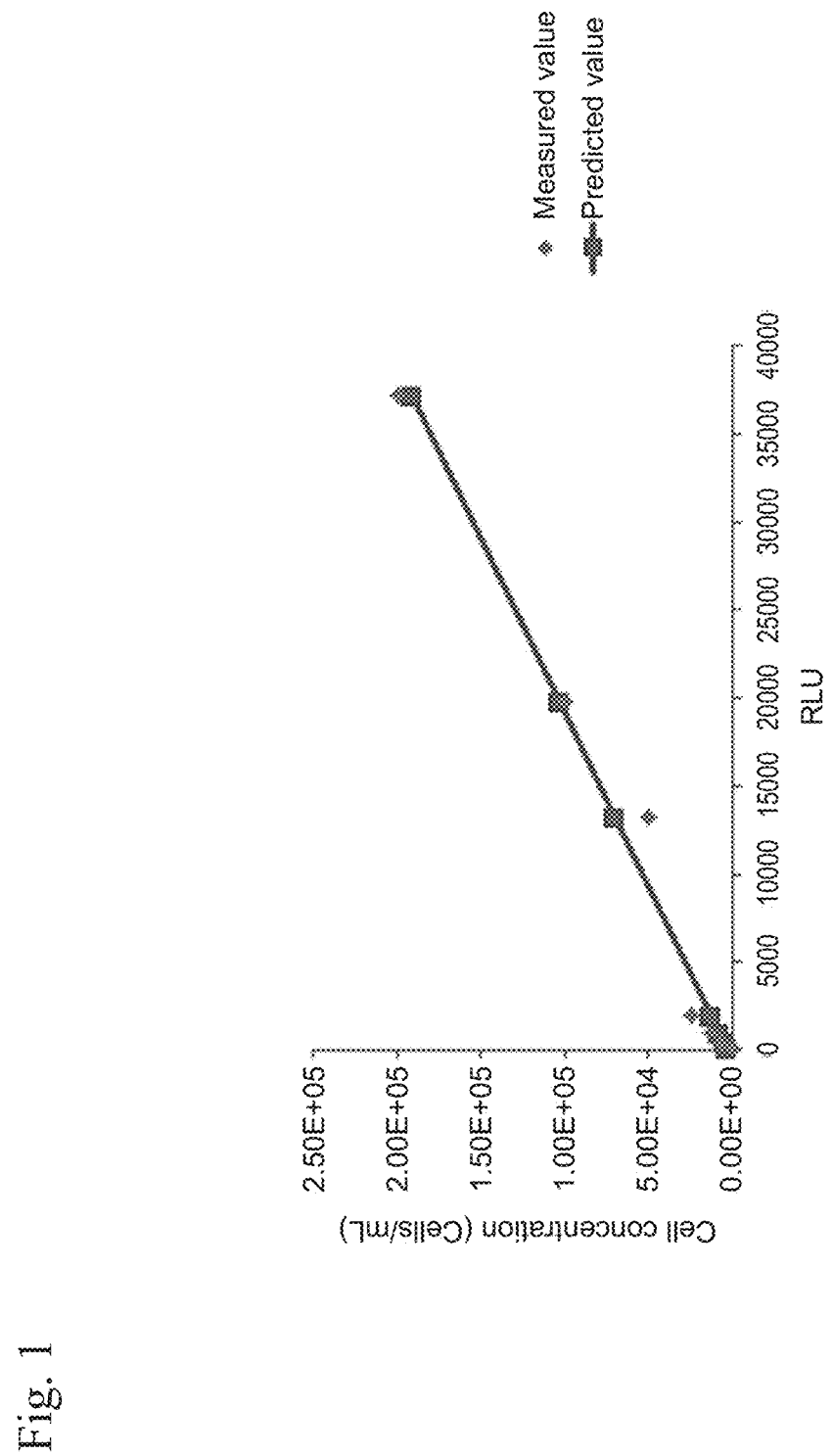
FIG. 1 is a characteristic chart indicating the results of single regression analysis of the cell concentration (Y) and the relative live cell signal (RLU) (X) of human PBMCs measured by CellTiter-Fluor Cell Viability Assay (Promega).

The present invention will be described in detail below.

According to the present invention, it has been found that a substance capable of inhibiting tyrosine kinase encoded by the ABL1 gene has an effect of specifically killing CD4+ T cells infected with HTLV-1 in CD4+ T cells from HTLV-1-associated myelopathy patients and CD4+ T cells from asymptomatic carriers (ACs). In other words, a substance capable of inhibiting tyrosine kinase encoded by the ABL1 gene can be used as a therapeutic agent for HTLV-1-associated myelopathy which is administered to HTLV-1-associated myelopathy patients for treatment of HTLV-1-associated myelopathy, and it can also be used as an anti-HTLV-1 drug which is administered to asymptomatic carriers of HTLV-1 in order to reduce the viral load. In addition, the therapeutic agent for HTLV-1-associated myelopathy according to the present invention also has an effect of reducing the viral load by specifically killing HTLV-1-infected CD4+ T cells as well as the therapeutic effects on HTLV-1-associated myelopathy.

In other words, the therapeutic agent for HTLV-1-associated myelopathy and the anti-HTLV-1 drug according to the present invention contain a substance capable of inhibiting tyrosine kinase encoded by the ABL1 gene as an active ingredient. The therapeutic agent for HTLV-1-associated myelopathy and the anti-HTLV-1 drug according to the present invention have the effect of specifically killing HTLV-1-infected CD4+ T cells.

The ABL1 gene has a nucleotide sequence and an amino acid sequence registered under accession nos. NM_005157 (NP_005148.2) and NM_007313(NP_009297.2), respectively, in the NCBI database. Note that the ABL1 gene is not limited to such specific nucleotide sequence and amino acid sequence registered in the database, and it may have a nucleotide sequence and an amino acid sequence different from the specific nucleotide sequence and amino acid sequence registered in the database due to a polymorphism such as a known single nucleotide polymorphism.

The substance capable of inhibiting tyrosine kinase encoded by the ABL1 gene is not particularly limited. It may be, for example, a drug capable of inhibiting production and/or activity of the tyrosine kinase or a drug capable of promoting degradation and/or inactivation of the tyrosine kinase. Examples of a substance capable of inhibiting the tyrosine kinase include, but are not particularly limited to, an RNAi molecule, a ribozyme, an antisense nucleic acid, and a DNA/RNA chimeric polynucleotide for the ABL1 gene encoding the tyrosine kinase, and a vector expressing any of them.

In addition, it is possible to use, as a substance capable of inhibiting the tyrosine kinase, a compound that acts on the tyrosine kinase. Examples of such compound that can be used include organic compounds (such as amino acids, polypeptides or derivatives thereof, low molecular compounds, sugars, and polymer compounds) and inorganic compounds. These compounds may be either natural substances or non-natural substances. Examples of derivatives of polypeptides include a modified polypeptide obtained by adding a modifying group and a variant polypeptide obtained by modifying an amino acid residue. Further, such compounds may be single compounds or may be compound libraries, gene library expression products, cell extracts, cell culture supernatants, fermented microbial products, marine organism extracts, plant extracts, and the like.

Specific examples of a substance capable of inhibiting tyrosine kinase encoded by the ABL1 gene include, but are not particularly limited to, imatinib, nilotinib, and dasatinib. Imatinib, nilotinib, and dasatinib are publicly known as tyrosine kinase inhibitors (TKIs) and used as, for example, therapeutic agents for chronic myelogenous leukemia. A substance capable of inhibiting trosine kinase encoded by the ABL1 gene is not limited to imatinib, nilotinib, and dasatinib. TKI as a substance currently under development or an investigational substance as a therapeutic agent for chronic myelogenous leukemia may be used.

It is possible to determine whether or not a certain substance functions to inhibit tyrosine kinase encoded by the ABL1 gene according to a conventional method. For example, a test compound is added to a solution containing tyrosine kinase encoded by the ABL1 gene and preincubated at 25° C. for 30 minutes. A biotinylated labeled substrate peptide (poly Glu-Tyr) and ATP are added to the preincubation solution to induce a phosphorylation reaction at 25° C. for 30 minutes. The reaction is terminated by adding EDTA and the reaction solution is added to an avidin-coated 96-well plate to allow the biotinylated substrate to bind to the plate. The phosphorylation level of the substrate is measured by ELISA using an anti-phosphorylated tyrosine antibody. In this assay system, it is preferable to use imatinib as a positive control. Based on the ELISA results, tyrosine kinase inhibitory activity in a test compound can be assayed by comparison with imatinib.

In addition to the above publicly known compounds, the following (1) to (3) may be used as a therapeutic agent for HTLV-1-associated myelopathy or an anti-HTLV-1 drug, which is a substance capable of inhibiting expression of the ABL1 gene or tyrosine kinase activity.

(1) Substance Capable of Inhibiting Translation of the ABL1 Gene (1-1) Double-Stranded RNA In order to inhibit the translation of the ABL1 gene, RNA interference can be used. Specifically, mRNA of the ABL1 gene is degraded by introducing double-stranded RNA complementary to the nucleotide sequence of the ABL1 gene as a target into cells, thereby specifically inhibiting gene expression in the cells. This technique has been also confirmed effective for mammalian cells and the like (Hannon, G J., Nature (2002) 418, 244-251 (review); JP Patent Publication (Kohyo) No. 2002-516062 A; JP Patent Publication (Kohyo) No. H8-506734 A (1996)). Conventional methods can be referred to for details of design, preparation, and administration of a double-stranded RNA (dsRNA) molecule for the ABL1 gene.

(1-2) Antisense Method

In addition, as means for suppressing the translation of the ABL1 gene, a method using a so-called antisense nucleic acid can be mentioned. Specifically, translation of mRNA of the ABL1 gene is suppressed by introducing DNA that transcribes antisense RNA to mRNA of the ABL1 gene as a plasmid or incorporating it into the genome of a subject and allowing the antisense RNA to be hyperexpressed. Techniques related to antisense RNA using, for example, mammals as hosts are also known (Han et al. (1991) Proc. Natl. Acad. Sci. USA. 88, 4313-4317; Hackett et al. (2000) Plant Physiol., 124, 1079-86).

(2) Substance Capable of Inhibiting Transcription of the ABL1 Gene

An example of a substance capable of inhibiting transcription of the ABL1 gene is an expression vector that can be used for replacing the transcription promoter region of the gene in a target subject with a transcription inhibiting promoter. In addition, as means for inhibiting transcription of the ABL1 gene, an expression vector for inserting a nucleotide sequence having transcription inhibiting activity into a region involved in transcription of the gene may be used. Design and preparation of expression vectors such as those as described above are well known to those skilled in the art.

(3) Antibody Against Tyrosine Kinase Encoded by the ABL1 Gene

An antibody against tyrosine kinase can specifically bind to tyrosine kinase so as to inhibit kinase activity of tyrosine kinase. An antibody against tyrosine kinase can be made by a method for producing an antibody known in the art. Briefly, an immunogen is prepared using a full-length protein of tyrosine kinase or a partial peptide thereof and the immunogen is administered to an appropriate animal (e.g., a mouse, rat, rabbit, goat, or bird) at an appropriate number of doses, thereby making it possible to induce an antibody against tyrosine kinase. A polyclonal antibody can be obtained by collecting antisera from the immunized animal. It is also possible to obtain a monoclonal antibody by fusing splenocytes or antibody-producing cells of the immunized animal with immortalized cells (such as myeloma cells) to prepare hybridomas, screening for a hybridoma that produces an antibody of interest, and collecting the antibody from the hybridoma. In addition to the above, chimeric antibodies, humanized antibodies, human antibodies, antibody fragments, and the like can also be used, and they can be prepared according to methods known in the art.

The above-mentioned substance capable of inhibiting tyrosine kinase encoded by the ABL1 gene acts on the pathway including the gene that is significantly and increasingly expressed in CD4+ T cells from HTLV-1-associated myelopathy patients in a suppressive manner, thereby achieving treatment of HTLV-1-associated myelopathy.

The therapeutic agent of the present invention can be administered to a subject with HTLV-1-associated myelopathy and a subject with suspected HTLV-1-associated myelopathy. Such subjects may be, for example, animals such as mammals and birds. Examples of mammals include humans, laboratory animals (such as mice, rats, monkeys, rabbits, and chimpanzees), pet animals (such as cats and dogs), and livestock animals (such as bovines, horses, sheep, goats, and pigs).

In addition, therapeutic effects of the therapeutic agent of the present invention include providing favorable effects on at least health of a subject who has received the agent, and preferably, reducing or alleviating at least one symptom of HTLV-1-associated myelopathy or preventing progression or recurrence of HTLV-1-associated myelopathy. Examples of symptoms of HTLV-1-associated myelopathy include, but are not limited to, gait disorder; urination/defecation disorder such as frequent urination, urination difficulty, urinary incontinence, or chronic constipation; sensation disturbance; sweating disorder; autonomic symptoms such as dizziness due to orthostatic hypotension and erectile dysfunction; finger tremor; ataxia; mild dementia; and spastic paresis of lower limbs.

The anti-HTLV-1 drug of the present invention can be administered to a subject who has not developed HTLV-1-associated myelopathy (i.e., an asymptomatic carrier (AC) having HTLV-1). Note that the anti-HTLV-1 drug of the present invention may be administered to a subject with HTLV-1-associated myelopathy and a subject with suspected HTLV-1-associated myelopathy so as to reduce the viral load. Such subjects may be, for example, animals such as mammals and birds. Examples of mammals include humans, laboratory animals (such as mice, rats, monkeys, rabbits, and chimpanzees), pet animals (such as cats and dogs), and livestock animals (such as bovines, horses, sheep, goats, and pigs).

In addition, in a case in which the anti-HTLV-1 drug of the present invention is administered to an asymptomatic carrier, it exerts an effect of reducing the viral load, which can be evaluated based on the HTLV-1 proviral load (PVL), and in particular, PVL only in live cells. This makes it possible to prevent an asymptomatic carrier of HTLV-1 from developing HTLV-1-associated myelopathy or adult T cell leukemia (ATL).

In particular, it has been known that the proviral load of HTLV-1-associated myelopathy is significantly higher than that in asymptomatic carriers (Nagai M. J. NeuroVirol 1998.4:586-593), and there are asymptomatic carrier cases who have high proviral loads but have not developed HTLV-1-associated myelopathy or adult T cell leukemia (ATL). In recent years, it has been reported that many asymptomatic carrier cases with high proviral loads developed HTLV-1-associated myelopathy, which may be a prognostic factor (Martins M L. et al. J. NeuroVirol. 2017. 23(1):125-133), and an epidemiological study revealed the development of adult T cell leukemia (ATL) in an asymptomatic carrier group with high proviral loads (4.17-28.58 copies/100 PBMCs) (Iwanaga M. et al. Blood 2010. 116(8): 1211-9). It is becoming a consensus that there are cases in which any kind of therapeutic intervention should be made even for asymptomatic carriers.

In the present state of HTLV-1-associated diseases for which there are substantially no antiviral drugs, the anti-HTLV-1 drug according to the present invention can be used as means of promising antiviral therapy.

The therapeutic agent and the anti-HTLV-1 drug of the present invention can be formulated with one or more pharmaceutically acceptable carriers or excipients in a conventional manner. For example, the therapeutic agent and the anti-HTLV-1 drug of the present invention can be formulated into a composition to be given via nasal administration, oral administration, rectal administration, or administration by injection. Administration may be performed in a systemic or localized manner.

The therapeutic agent and the anti-HTLV-1 drug of the present invention may be in any dosage form depending on the administration route, for example, in the form of a solution, a suspension, an emulsion, tablets, pills, pellets, capsules, a powder, a sustained release preparation, a suppository, an aerosol, or a spray.

For nasal administration, an active ingredient can be delivered by dissolving it in an appropriate solvent (e.g., physiological saline or alcohol) and injecting or dropping the solution into the nose. Alternatively, for nasal or inhalation administration, an active ingredient can be conveniently delivered by ejecting an aerosol spray from a pressurized pack or nebuliser with an appropriate aerosolized agent, for example, a gas of dichlorodifluoromethane, trichlorofluoromethane, dichlorotetrafluoroethane, carbon dioxide, or the like. In the case of pressurized aerosol spraying, the dosage unit can be determined by providing a valve that allows the measured dose to be delivered.

In the case of injection, an active ingredient can be formulated as a solvent for parenteral administration (i.e., intravenous or intramuscular administration) by, for example, bolus injection or continuous infusion, and preferably, it can be formulated as a physiologically compatible buffer such as a Hank's solution, a Ringer's solution, or physiological saline. The solvent may contain prescribable agents such as a suspending or stabilizing agent and/or a dispersing agent. Alternatively, an active ingredient can be in a powder form for reconstitution with a suitable excipient, for example, sterile pyrogen-free water before use. A formulation for injection can be provided in a unit dosage form, for example, in an ampule or a multi-dose container with the addition of a preservative.

In the case of oral administration, the therapeutic agent and the anti-HTLV-1 drug of the present invention can be in the form of, for example, tablets, lozenges, an aqueous or oily suspension, a granule, a powder, an emulsion, capsules, a syrup, or an elixir. In a case in which a composition is in the form of tablets or pills, the composition can be coated to delay dispersion and absorption in the gastrointestinal tract, thereby providing a sustained action over a long period of time.

Formulation forms and formulation methods suitable for other administration routes are known in the art. It is possible to arbitrarily select a formulation form and a method from them to produce the therapeutic agent and the anti-HTLV-1 drug of the present invention.

Examples of a pharmaceutically acceptable carrier or excipient include, but are not limited to, liquids (e.g., water, oil, physiological saline, an aqueous dextrose solution, and ethanol), solids (e.g., gum acacia, gelatin, starch, glucose, lactose, sucrose, talc, sodium stearate, glycerol monostearate, keratin, colloidal silica, dried skimmed milk, and glycerol). In addition, the therapeutic agent of the present invention may contain an additive, a preservative, a stabilizer, a thickener, a lubricant, a colorant, a wetting agent, an emulsifier, and/or a pH buffering agent which may be formulated in conventional pharmaceutical compositions if appropriate.

The therapeutic agent and the anti-HTLV-1 drug of the present invention contain an effective dose of a substance capable of inhibiting tyrosine kinase encoded by the ABL1 gene. The effective dose means a sufficient amount of an active ingredient for providing favorable effects on the health of a subject to be treated.

Toxicity and therapeutic efficacy of the therapeutic agent and the anti-HTLV-1 drug of the present invention can be determined in a cell culture product or a laboratory animal by standard procedures in order to determine, for example, LD50 (dose lethal for 50% of a population) and ED50 (dose therapeutically effective for 50%6 of a population). The ratio of a dose showing toxic effects to a dose showing therapeutic effects is a treatment index which can be expressed as an LD/ED ratio.

It is preferable for the therapeutic agent and the anti-HTLV-1 drug to have a high treatment index. In the case of high toxicity, it should be noted that a delivery system, by which the therapeutic agent and the anti-HTLV-1 drug are targeted at the site of affected tissue, is designed in order to minimize possible damage on non-affected cells, thereby reducing side effects.

The range of doses for use in humans can be determined using data obtained from cell culture assay and animal tests. Such doses of the therapeutic agent and the anti-HTLV-1 drug are preferably within a range of circulating plasma concentrations including ED50 achieving no or substantially no toxicity. The dosage varies within such range, depending on the dosage form and the route of administration used herein. Regarding the therapeutic agent and the anti-HTLV-1 drug of the present invention, their effective doses can be estimated from cell culture assay. The effective dose in an animal model can be determined such that it falls within the range of circulating plasma concentrations including IC50 determined by cell culture (i.e., the concentration of a therapeutic agent to be tested at which up to half of symptoms can be suppressed). Such information can be used to determine the effective dose in humans in more detail. Plasma levels can be measured by, for example, high performance liquid chromatography.

Those skilled in the art can select appropriate doses of the therapeutic agent and the anti-HTLV-1 drug of the present invention depending on subject's symptoms and age and/or administration routes. For example, in a case in which imatinib is used for the therapeutic agent and the anti-HTLV-1 drug of the present invention, the dosage can be set to a level similar to that for treatment of chronic myelogenous leukemia.

EXAMPLES

The present invention will be described in more detail by the Examples described below. However, the technical scope of the present invention is not limited thereto.

Example 1

As mentioned in Experimental Example 1 described below, as a result of microarray analysis and pathway analysis using CD4+ T cells from HTLV-1-associated myelopathy (HAM) patients, pathways including the ABL1 gene were identified as pathways including a gene with a significantly increased expression level in CD4+ T cells from HAM patients. In this Example, imatinib (Glivec/Gleevec) and nilotinib (Tasigna), which are inhibitors of tyrosine kinase encoded by the ABL1 gene, were used to examine the influence of these drugs on CD4+ T cells from HAM patients.

<Examination Method>

[1] Measurement of the cell concentration of human PBMCs (assay sensitivity determination) by CellTiter-Fluor Cell Viability Assay (G6080, Promega Corporation) (# TB (Technical Bulletin) 371: Instructions for use of Products G6080. G6081, and G6082 (Promega)) (This kit is to quantify the intensity of fluorescence derived from cleavage of a GF-AFC substrate by live cell protease, which is proportional to the number of live cells, using glycylphenylalanyl-amino-fluoro coumarin (GF-AFC, Ex400/Em505 nm) as a cell membrane permeable fluorescent peptide serving as a substrate of live cell protease)

(1) Protocol (1-1) Cell washing: A peripheral blood mononuclear cell (PBMC) specimen ($1 \times 10^7$ cryopreserved cells in liquid nitrogen) from a relatively fresh negative control (NC) was dissolved in a water bath at 37° C. and transferred to a 15-mL tube containing 10 mL of PBS, and the solution was centrifuged at 300×g for 10 minutes and washed. The supernatant was discarded, pellets exclusively remaining on the bottom of the tube were scraped with a wire mesh, and 10 mL of PBS was added to perform washing again. Then, 1 mL of PBS was added for suspension, and the tube was placed on ice.

(1-2) Determination of the cell concentration by a hemocytometer and adjustment of the cell specimen concentration: The live cell concentration was determined using a Burker-Turk hemocytometer and a 0.4% trypan blue solution (T8154, Sigma-Aldrich Japan) by the trypan blue-exclusion test. The concentration of live cells was diluted such that the number of cells was adjusted to 400,000 ($4 \times 10^5$) cells/mL (medium) in a RPMI1640 medium (#189-02025 Wako Pure Chemical Industries, Ltd.) supplemented with 10% inactivated fetal bovine serum (#10437028, Thermo Fisher Scientific Inc.) and 1% penicillin-streptomycin (#15140122, Thermo Fisher Scientific Inc.).

(1-3) Plating on a 384-well plate: A 384-well plate such as a Nunc 384-well clear polystyrene plate with non-treated surface (#242765, Thermo Fisher Scientific) was prepared, and 20 μL of a cell suspension ($1 \times 10^4$ cells) adjusted to have a cell concentration of $5 \times 10^5$ cells/mL (medium) was placed in 12 wells of the 1st to 3rd and 7th to 9th columns (6 columns in total) of rows A and B by pipetting with a multichannel pipettor.

Next, 25 μL of the above medium was placed in wells of the 1st to 3rd and 7th to 9th columns of rows B to H. Since each well in row B contained 20 μL of the mixture of the cell suspension and the medium, pipetting was performed by a multichannel pipettor while avoiding foaming, and 10 μL of the mixture in each well of row B was transferred to the corresponding well of row C. Similarly, 10 μL of the mixture was transferred from the upper row to the lower row, for example, from row C to row D, from row D to row E, row E to row F. and row F to row G row in that order. From the wells of row G, 10 μL of the mixture was suctioned and discarded. The cell suspension from row G was not added to row H to prepare no-cell controls.

By the above operation, the cell concentrations in rows A to G and row H row were adjusted to 10.000 cells, 5,000 cells, 2,500 cells, 1,250 cells, 625 cells, 312.5 cells, 156.25 cells, and 0 cells (no-cell control), respectively, and the liquid volume in every well was adjusted to 10 μL.

(1-4) Cell killing by digitonin: A solution of DMSO (043-07216, Wako Pure Chemical Industries, Ltd.) containing digitonin (Calbiochem #300410, Merck-Millipore) serving as a cytolytic detergent at 20 mg/mL was prepared as a stock solution. The solution was further diluted with DMSO to prepare a 300 μg/mL digitonin working solution. The digitonin working solution in a volume of 2.5 μL was added to each of the wells of the 7th to 9 columns of rows A to H of the above 384-well plate. The wells were prepared for fluorescent signals of dead cells.

In order to standardize the liquid volume, 2.5 μL of double distilled water (D2 W) was added as a sample untreated with digitonin (control) to wells of the 1st to 3rd columns of rows A to H. Accordingly, the liquid volume of each well was set to 12.5 μL.

(1-5) Addition of a CellTiter-Fluor 2× reagent: CellTiter-Fluor 2× reagent (G6080, Promega Corporation) was added in a volume of 12.5 μL to all wells of the 1st to 3rd and 7th to 9th columns of rows A to H. Specifically, the liquid in a volume of 12.5 μL and the 2× reagent were mixed at a volume ratio of 1:1 in each well.

After mixing for a short time on an orbital shaker, the plate was incubated in an incubator at 37° C. for 30 minutes. The 2× reagent was prepared by dissolving a GF-AFC substrate and assay buffer at a volume ratio of 1:1000 by vortexing until the substrate was completely dissolved.

(1-6) Fluorometry: Fluorometry was performed by TECAN Infinite 200 M (Tecan Japan Co., Ltd.) (Ex400/Em 505 nm).

(1-7) Regression analysis of fluorescent signals and cell concentrations: The live cell signal ratio was calculated for each dilution (cell concentration) by the following formula using the live cell signals (of untreated samples) and dead cell signals (of treated samples) measured in (1-6) above.

Relative live cell signal (RLU)=[Live cell signal–Dead cell signal]/(Average no-cell control signal)

A regression formula was created by single regression analysis using cell concentrations as explanatory variables and live cell signal ratios as target variables. The cell concentration of the original cells was calculated from CellTiter Fluor signals of the same cells using the created regression formula.

(1-8) Calculation of sensitivity: Sensitivity was determined by calculating a signal-to-noise ratio (S/N ratio) for each cell dilution (10,000 cells/well; 5,000 cells/well; 2,500 cells/well, or the like). Note that the actual level of assay sensitivity is said to have an S/N ratio greater than 3 SD (Niles, A. L. et al. (2007) A homogeneous assay to measure live and dead cells in the same sample by detecting different protease markers. Anal. Biochem. 366, 197-206).

Viability S:N=[Average of untreated samples–Average of treated samples]/(Standard deviation from H-1 to H-3)

(2) Results

The relationship between the measured RLU and the cell concentration is indicated in Table 1.

TABLE 1

| RLU | Cell concentration (cells/mL) |
|---|---|
| 37154.33 | 2.00E+05 |
| 19791.67 | 1.00E+05 |
| 13279 | 5.00E+04 |
| 1968 | 2.50E+04 |
| 998.67 | 1.25E+04 |
| 487 | 6.26E+03 |
| 163.33 | 3.12E+02 |

In addition, the results were used for performing single regression analysis using RLU as an explanatory variable (X) and the cell concentration as a target variable (Y). As a result, the following regression formula was obtained: Y=5.092279X+2578.274, P=2.369E-05, R2=0.9890997. FIG. 1 is a graph of the regression formula of RLU (X) and the cell concentration (Y). In this Example, it was determined to calculate the cell concentration of PBMCs from fluorescent signal data by this regression formula.

[2] Determination of Cell Death Inducing Effects of ABL1 Inhibitor Treatment on HAM-Derived CD4+ T Cells In this section, it was examined whether cell death of PBMCs derived from HAM patients occurs more preferentially than cell death of NC-derived PBMCs by treating the PBMCs derived from HAM patients using ABL1 inhibitors (imatinib (Glivec/Gleevec™) and nilotinib). Note that in this section, it was decided to examine imatinib and nilotinib at a high concentration (5 μM) based on the Cmax concentration in the package insert of imatinib.

(2-1) Protocol

[Specimen]

Cryopreserved PBMCs in liquid nitrogen, which were 5×10$^6$ cells from 6 HAM patients and 6 negative controls (NCs), were prepared.

[Preparation of Cells]

PBMCs thawed in a water bath at 37° C. were transferred to a 15 mL tube containing 10 mL of PBS, centrifuged at 300×g for 10 minutes, and washed. The supernatant was discarded, pellets exclusively remaining on the bottom of the tube were scraped with a wire mesh, and 10 mL of PBS was added to perform washing again.

PBMCs were separated into CD4+ T cells and non-CD4-PBMCs according to the protocol of CD4+ T cell isolation kits for humans (#130-096-533, Miltenyi Biotec) using microbeads and an antibody cocktail. The separated cells were resuspended in 6.5 mL of PBS and each tube was placed on ice.

[Drug Treatment]

ABL1 inhibitors: Cell death inducing effects of imatinib and nilotinib were verified by cell concentration measurement using CellTiter-Fluor Cell Viability Assay (G6080. Promega Corporation).

First, PBS suspensions of CD4+ T cells and non-CD4-PBMCs from each specimen were thoroughly mixed while vortexing, and each mixture was placed in triplicate wells (2,000 μL each) of a Falcon 6-well clear flat-bottom TC-treated multiwell cell culture plate with-lid (#353046, Corning Japan K.K.). Note that each set of triplicate wells was prepared to consist of a well without drug treatment, a well treated with imatinib (final concentration: 5 μM), and a well treated with nilotinib (final concentration: 5 μM). Stock solutions (DMSO solutions) of imatinib and nilotinib with sufficiently high concentrations were prepared. The final concentration of each solution was adjusted to ¹⁄₁₀₀₀. The cell concentrations in triplicate wells at the start of incubation were considered to be the same.

Next, the cells were incubated at 37° C. under 5% $CO_2$ for 24 hours, and the whole cell suspension in each well was harvested 24 hours later. Each tube containing a cell suspension of CD4+ T cells in a well without drug treatment was mixed while vortexing, and a HAM specimen 1-derived CD4+ T cell suspension was placed in a volume of 25 μL into triplicate wells of the 1st column of rows A to C of a Nunc 384-well clear polystyrene plate with non-treated surface (#242765, Thermo Fisher Scientific). Similarly, a HAM specimen 2-derived CD4+ T cell suspension was placed in the 2nd column of rows A to C and a HAM specimen 3-derived cell suspension was placed in the 3rd column of rows A to C in that order in a manner such that a HAM specimen 6-derived cell suspension was eventually placed in the 6th column of rows A to C. In addition, an NC specimen 1-derived cell suspension was placed in the 7th column of rows A to C. Similarly, suspensions were placed in a sequential manner, and the last NC specimen 6-derived cell suspension was placed in the 12th column of rows A to C.

Likewise, also for non-CD4-PBMCs, cell suspensions from HAM specimens 1 to 6 and NC specimens 1 to 6 were placed in the 1st to 12th columns of rows D to F. In the 1st to 12th columns of row G, 25 μl of PBS was added as a no-cell control.

Subsequently, 25 μL of the CellTiter-Fluor Reagent was added to every well and mixed for a short time on an orbital shaker. Then, the plate was incubated in an incubator at 37° C. for at least 30 minutes under light protection. Thereafter, fluorometry was performed by TECAN Infinite 200 M (Tecan Japan Co., Ltd.) (Ex 400/Em 505 nm).

Meanwhile, in order to perform fluorometry of HAM specimens 1 to 6 and NC specimens 1 to 6 in the same manner, another plate was prepared for imatinib-treated CD4+ T cells/non-CD4-PBMCs (final concentration: 5 μM), and also another plate was prepared for nilotinib-treated CD4+ T cells/non-CD4-PBMCs (final concentration: 5 μM).

The number of live cells (absolute value) was calculated. The number of live cells before exposure was regarded as 100%, and the number of live cells after 24 hours was regarded as X % in the case of no exposure (24 hours after exposure in the case of exposure). The percent reduction of the number of cells (% REGRESSION) was compared for the case of no exposure, for the case of exposure to imatinib, and the case of exposure to nilotinib.

(2-2) Control Experimentation

For comparison, time-dependent changes in the cell concentration upon in vitro culture of HAM-derived CD4+ T cells, NC-derived CD4+ T cells, and non-CD4-PBMC were confirmed. Specifically, PBMCs were separated into CD4+ T cells and non-CD4-PBMCs for 3 HAM cases and 2 NC cases, and then, approximately $8 \times 10^4$ cells in 2 mL of RPMI1640 medium (drug-free) on a 6-well plate were observed over time.

The cell concentration was observed by the trypan blue-exclusion method at the start of observation (0 h), 24 hours later (24 h), and 48 hours later (48 h). The concentration at 0 h was regarded as 100% and expressed as the relative concentration of each sample.

(2-3) Results

Figure 2:
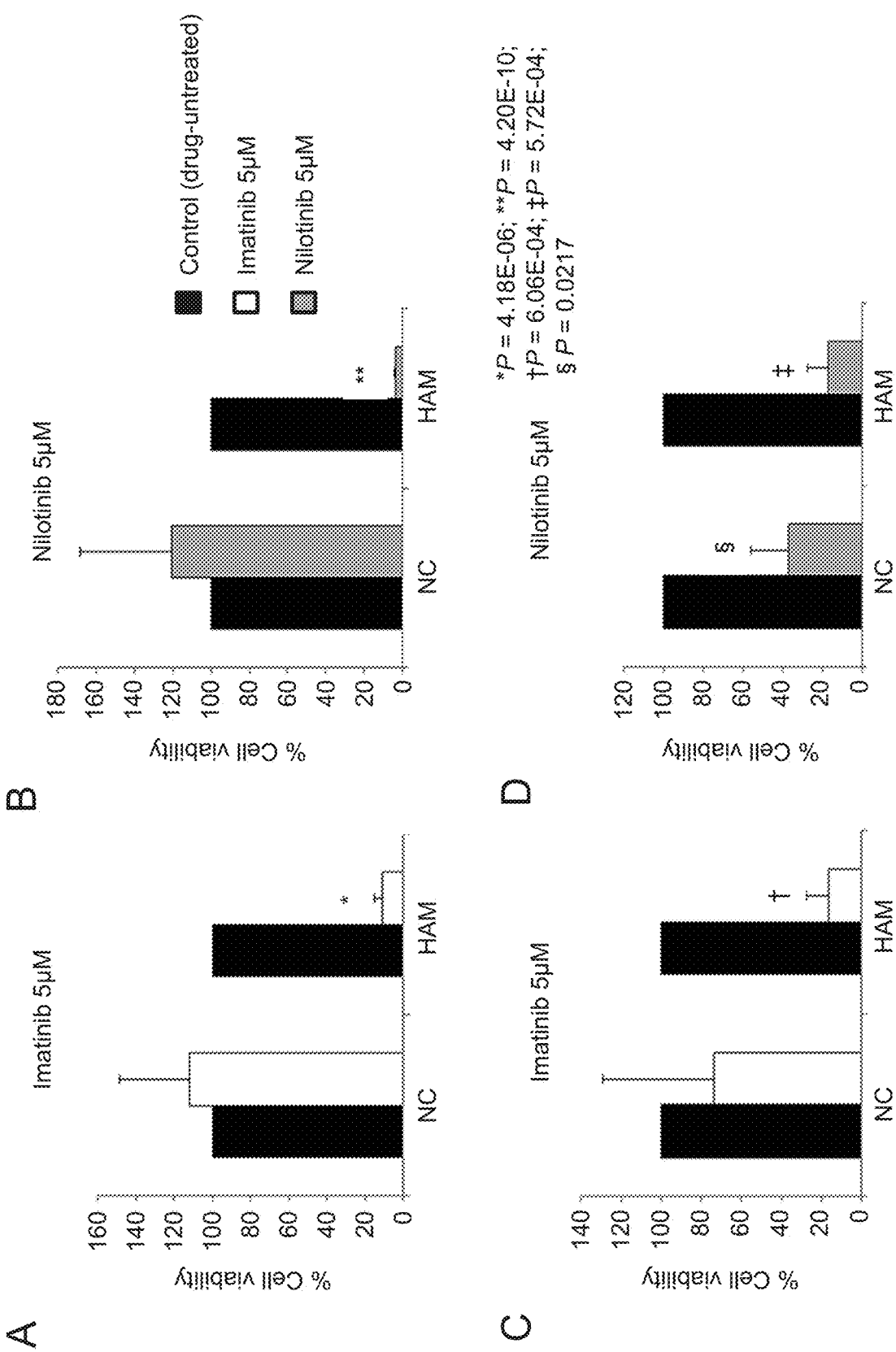
FIG. 2 depicts characteristic charts indicating the effects of ABL1 inhibitors (imatinib and nilotinib) on cell viability.

FIG. 2 depicts the effects of 24-hour treatment with ABL1 inhibitors (5 μM imatinib and 5 μM nilotinib) on cell viability. Chart A of FIG. 2 depicts the effects of 24-hour treatment with 5 μM imatinib on cell viability of CD4+ T cells. Chart B of FIG. 2 depicts the effects of 24-hour treatment with 5 μM nilotinib on cell viability of CD4+ T cells. Chart C of FIG. 2 depicts the effects of 24-hour treatment with 5 μM imatinib on cell viability of non-CD4-PBMCs. Chart D of FIG. 2 depicts the effects of 24-hour treatment with 5 μM nilotinib on cell viability of non-CD4-PBMCs.

As depicted in charts A and B of FIG. 2, it is understood that both imatinib and nilotinib cause cell death to occur in HAM-derived CD4+ T cells while cell death does not occur in NC-derived CD4+ T cells. Meanwhile, as depicted in charts C and D of FIG. 2, cell death of non-CD4-PBMCs was significantly observed for HAM in the case of imatinib and for both HAM and NC in the case of nilotinib.

Figure 3:
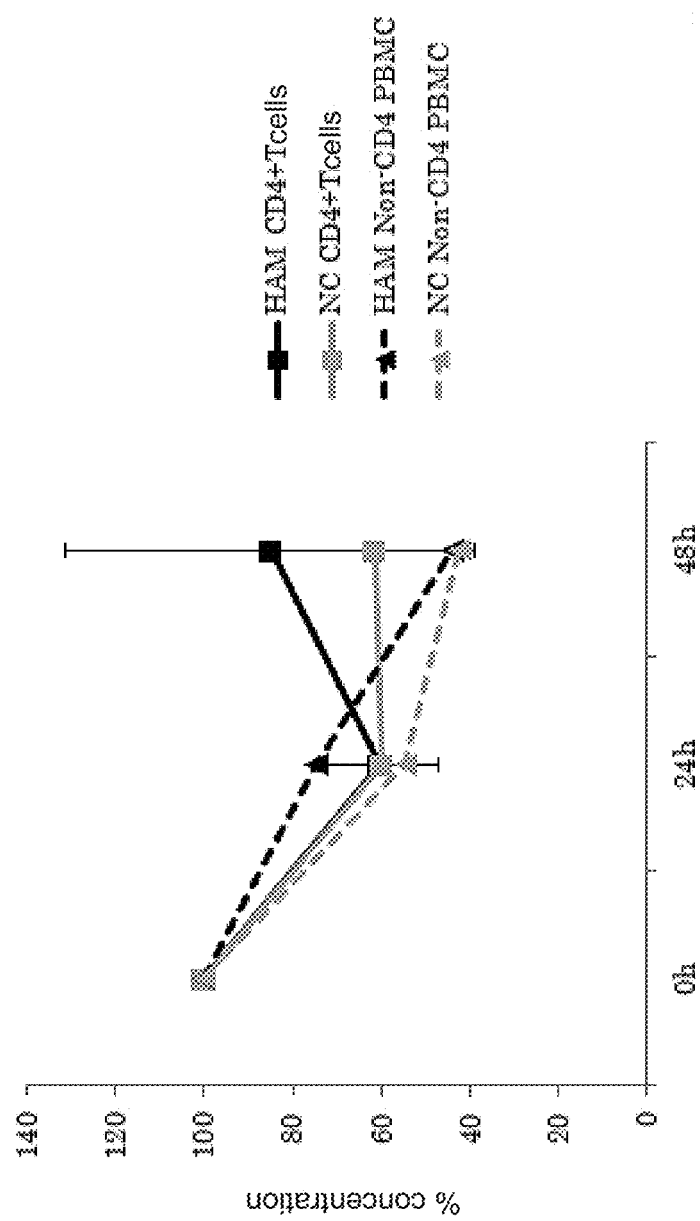
FIG. 3 is a characteristic chart indicating time-dependent changes in the cell concentration during in vitro culture of HAM, NC-derived CD4+ T cells, and non-CD4 PBMC.

Meanwhile, FIG. 3 depicts the results of control experimentation described in (2-2) above. As depicted in FIG. 3, the number of cells decreased over time for 24 hours and did not significantly vary until 48 hours later for HAM-derived non-CD4-PBMCs, NC-derived CD4+ T cells, and non-CD4-PBMCs. However, it is understood that HAM-derived CD4+ T cells tend to increase between 24 hours and 48 hours later.

(3) Discussion

Accordingly, it was revealed that both imatinib and nilotinib have an effect of preferentially killing CD4+ T cells from HAM patients. The preferential killing effect of ABL1 inhibitors on CD4+ T cells from HAM patients including HTLV-1-infected CD4+ T cells has not been reported so far and it has been discovered for the first time in the world. The ABL1 gene was extracted as a HAM treatment target from the array data described in detail below, suggesting the results confirming the correctness of this conclusion.

In control experimentation, as a result of observation without drug treatment over time, CD4+ T cells from HAM patients tended to increase between 24 hours and 48 hours later in a drug-free state. In consideration of this fact, the effect of reducing CD4+ T cells from HAM patients by ABL1 inhibitor treatment may be further revealed as a result of long-term time-dependent observation.

Meanwhile, the effect of cell death of non-CD4-PBMCs is suspected to be a side effect due to a clinically non-applicable high concentration (5 μM). Existing data on imatinib and/or nilotinib can be used as data on side effects of cytotoxicity at usual clinically applicable concentrations.

Experimental Example 1

Figure 4:
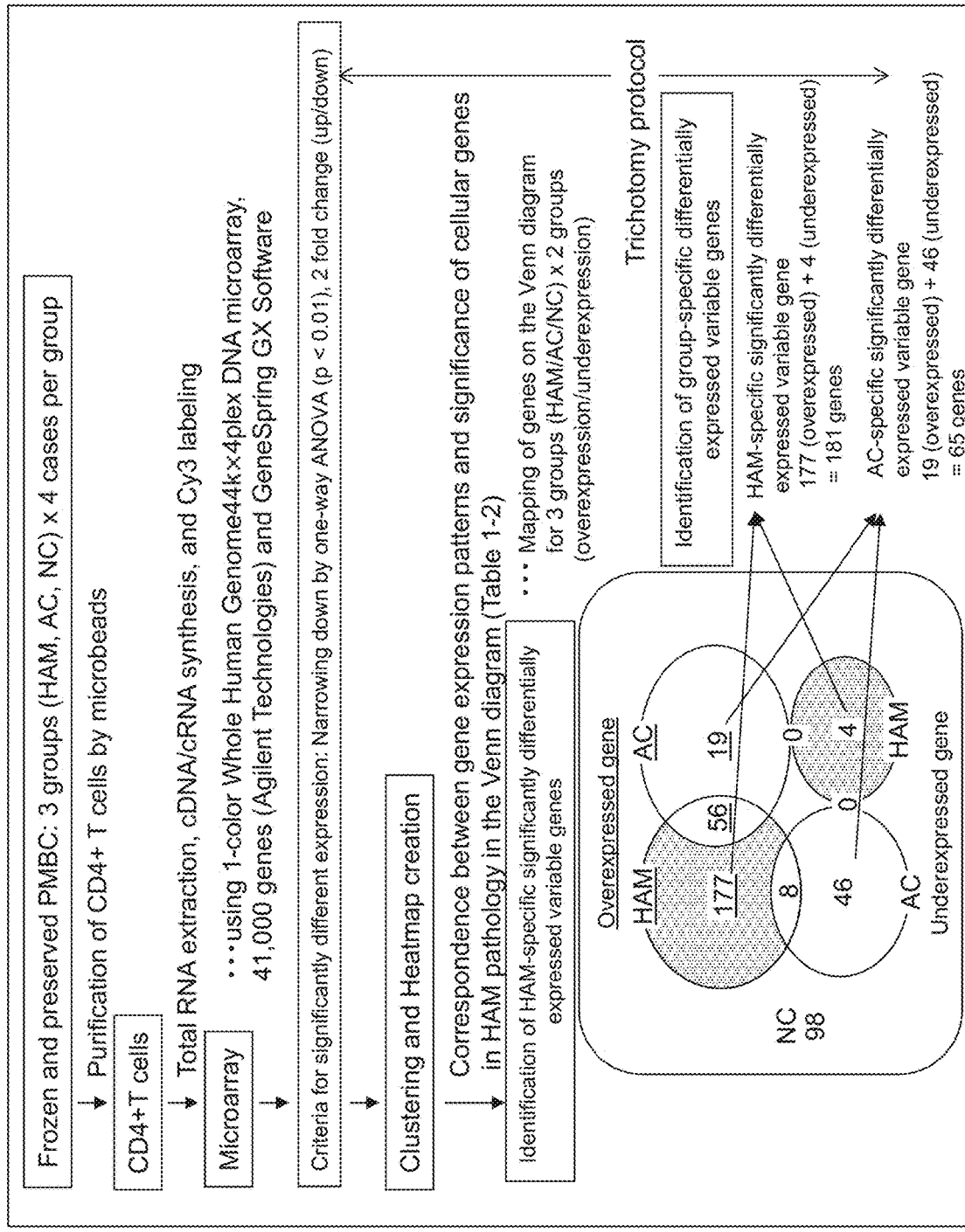
FIG. 4 is a flowchart of a method for identifying HAM-specific significantly differentially expressed genes by the trichotomy protocol for microarray data using CD4+ T cells from HAM patients.

In Experimental Example 1, pathways including genes significantly and increasingly expressed in CD4+ T cells from HTLV-1-associated myelopathy patients were identified by microarray analysis and pathway analysis using CD4+ T cells from HTLV-1-associated myelopathy patients. FIG. 4 depicts the flowchart of the analysis method in this experiment.

<Subjects>

Based on clinical diagnosis according to the WHO diagnostic criteria, 4 cases of HTLV-1-associated myelopathy patients, 4 cases of asymptomatic HTLV-1 carriers (ACs), and 4 cases of HTLV-1 negative healthy controls (NCs) were randomly selected (Table 2). In consideration of ethical issues, blood collection and specimen preservation were carried out with sufficient explanation and written consent. In this study, patients and specimens were anonymized in an unlinkable manner, and specimens obtained under approval from the Ethics Committee of Kagoshima University were used.

TABLE 2

|  | HAM | AC | NC |
|---|---|---|---|
| Number of specimens | 4 | 4 | 4 |
| Gender (Male:Female) | 2:2 | 1:3 | 2:2 |
| Age (average ± SE) (years old) | 60.0 ± 7.4 | 52.3 ± 4.9 | 52 ± 13.9 |
| Proviral load (copies/10⁴ PBMC) | 2066 ± 403.0 ←*→ | 325.8 ± 155.3 | — |
| Preservation period (average ± SE) (years) | 4.3 ± 0.0 | 2.2 ± 0.2** | 5.1 ± 1.1 |

*P = 0.021 (Mann-Whitney);
**P = 0.030 (Kruskal-Wallis)

<Selection of CD4+ T Cells from Frozen PBMC Specimens and Microarray>

Frozen specimens each containing approximately $2\times10^7$ PBMCs were used for harvesting CD4+ T cells. Further, extraction of total RNA, synthesis of cDNA, synthesis of Cy3-labeled cRNA and labeling (Cy3-CTP,633 nm excitation), purification of Cy3-labeled cRNA, and DNA microarray (1-color Whole Human Genome 44k×4-plex DNA microarray, 41,000 genes (Agilent Technologies)) were carried out, followed by hybridization and washing. Thereafter, images were obtained by the Agilent Microarray scanner, and then, raw data of quantified fluorescence signal intensities were acquired using Feature Extraction Software Ver. 10.5. In addition, logarithmic transformation and normalization of numerical data were carried out using GeneSpring GX software.

<Array Data Analysis Method>

(1) Extraction of Significantly Differentially Expressed Genes and Significant Pathways by Pathway Analysis (1-1) Criteria for Significantly Differentially Expressed Genes (Three-Group One-Way ANOVA)

Genes with a variation not less than a 2-fold change (up/down) as compared with NC and satisfying a requirement of p<0.01 in three-group one-way ANOVA were narrowed down as significantly differentially expressed genes. Significantly differentially expressed genes for HAM alone, AC alone, or both HAM and AC were searched for.

(1-2) Clustering and Heatmap Creation

Figure 5:
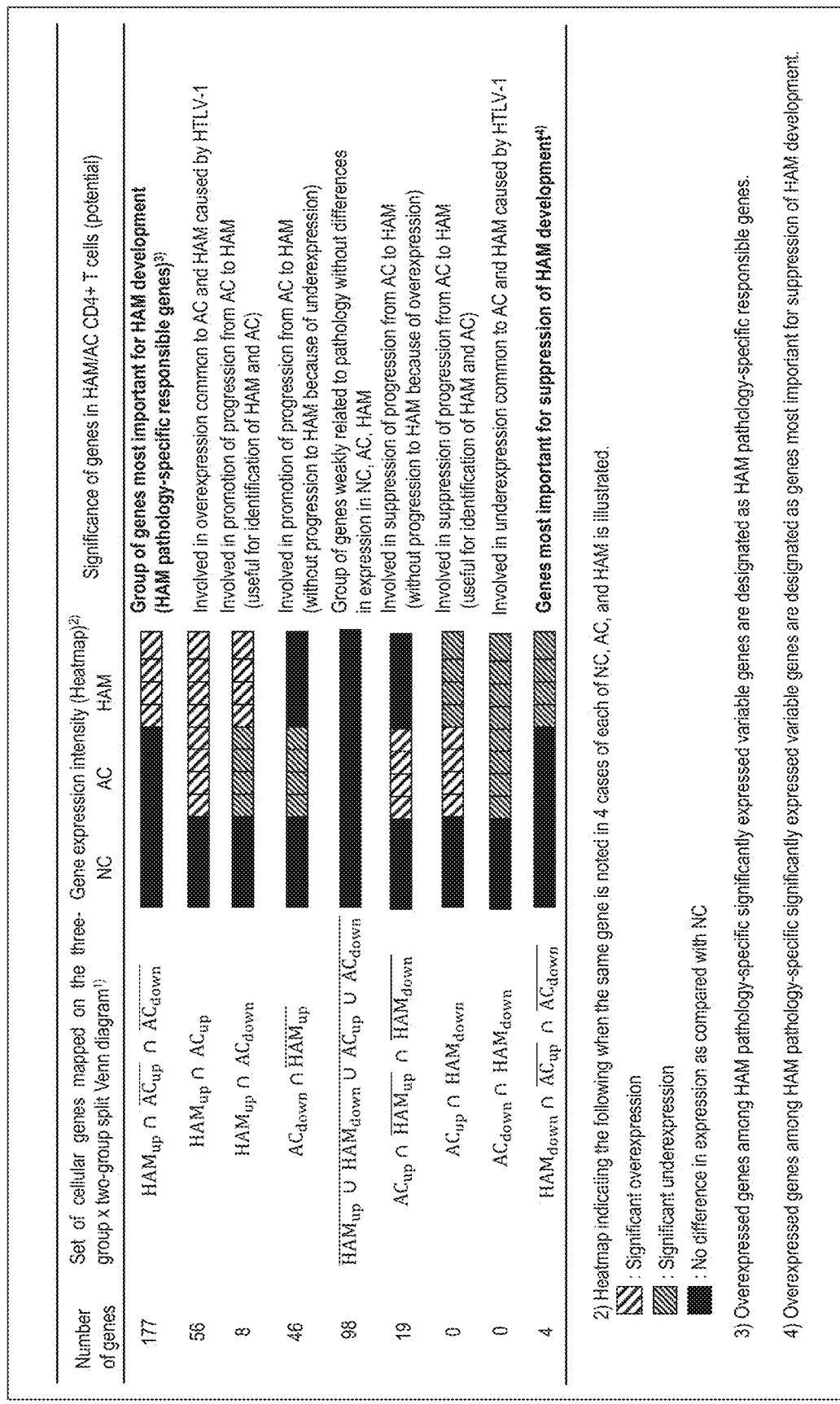
FIG. 5 is a characteristic chart indicating correspondence between gene expression patterns in HAM, AC, and NC and significance of cellular genes in HAM pathology.

FIG. 5 depicts the results of examination of the correspondence between gene expression patterns in HAM, AC, and NC and significance of cellular genes in HAM pathology. In 1) in FIG. 5, the three-group (HAM/AC/NC)×two-group (overexpression/underexpression) split Venn diagram is based on gene expression intensities of negative controls (NCs). Therefore, genes are roughly divided into 4 groups (2×2) in practice. $HAM_{up}$, $HAM_{down}$, $AC_{up}$, and $AC_{down}$ represent a gene overexpressed in HAM, a gene underexpressed in HAM, a gene overexpressed in AC, and a gene underexpressed in AC, respectively. Sets indicated by subscripts of up (overexpression) and down (underexpression) are underlined and not underlined, respectively, in the Venn diagram of FIG. 4. Array data were clustered (cluster analysis) and Heatmap was created.

(1-3) Novel Trichotomy Protocol Based on the Correspondence Between the Three-Group (HAM/AC/NC)×Two-Group (Overexpression/Underexpression) Split Venn Diagram and Heatmap A three-group (HAM/AC/NC)×two-group (overexpression/underexpression) split Venn diagram was further created, which was newly designed to display differentially expressed genes in a Venn diagram by three-group comparison in the case of viral infection or the like.

The correspondence between gene expression patterns in HAM, AC, and NC and significance of cellular genes in HAM pathology was replaced by the procedures of mapping on the Heatmap and the three-group (HAM/AC/NC)×two-group (overexpression/underexpression) split Venn diagram. Thus, 177 genes overexpressed only in HAM were identified as HAM pathology-specific responsible genes corresponding to the following formula in the Venn diagram.

$$HAM_{up} \cap \overline{AC_{up}} \cap \overline{AC_{down}}$$ [Formula 1]

FIGS. 6 to 11 depict the identified genes.

A method for extracting a series of pathology-specific responsible genes by three-group comparison employed in this section is a new method different from comparison by two-group t-test and referred to as "trichotomy protocol."

(1-4) Pathway Analysis

Figure 12:
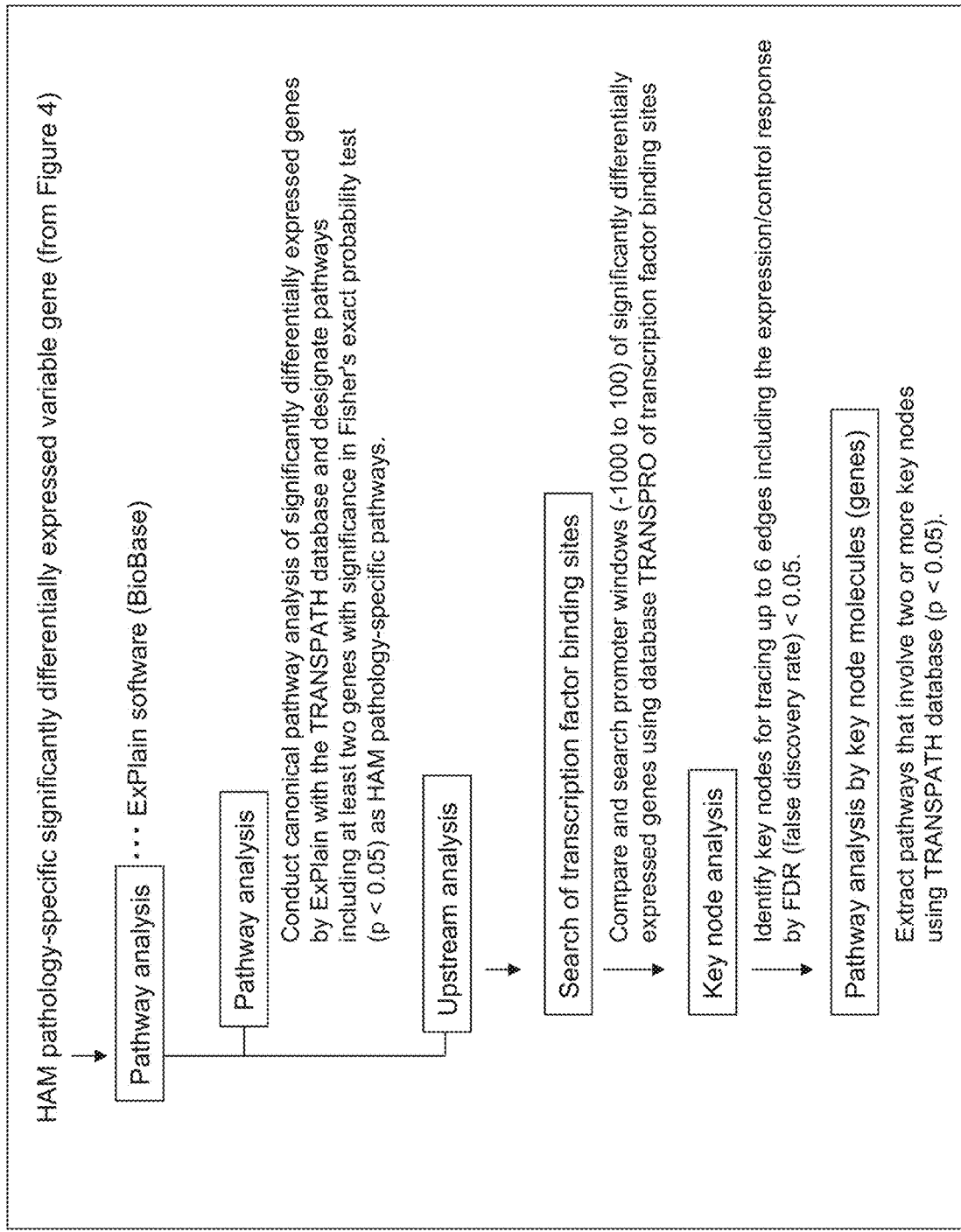
FIG. 12 is a flowchart of pathway analysis and a method for identifying HAM pathology-specific pathways.

FIG. 12 depicts the workflow of pathway analysis. A pathway including at least two significantly differentially expressed genes (# at least two Hits in group) was determined to be significant (P<0.05) using pathway analysis software ExPlain and pathway database TRANSPATH maintained by curators based on literature information (both are manufactured by BIOBASE GmbH).

(2) Upstream Analysis (2-1) Search of Transcription Factor Binding Sites

Promoter windows of significantly differentially expressed genes (−1000 to +100) were compared and searched using TRANSPRO, which is a database of transcription factor binding sites (elements), weighted consensus sequences were calculated and upstream transcription factors were predicted. In order to search for a gene group with a variation (Yes-set): fold change ≥2.0, a gene group without a variation (No-set): fold change <1.1, and a group of genes common in lack of variation in HAM, AC, and NC groups, 300 genes with lower coefficients of variation (C.V., a value obtained by dividing a standard deviation by an arithmetic average (the following formula) and yielding a unitless number representing a relative variation) were employed.

$$C.V. = \frac{\sqrt{\sigma^2}}{\bar{x}}$$ [Formula 2]

In addition, those satisfying a Yes/No site frequency ratio of >1.5, an accidental probability (P<0.05) for the number of binding sites existing in the Yes-set, and an accidental probability (p<0.05) for the number of promoters in the Yes-set were designated as transcription factor-binding sites.

(2-2) Key Node Analysis

Key nodes for tracing up to 6 edges including the expression/control response in the Yes-set were searched for based on FDR (False Discovery Rate)<0.05.

(2-3) Pathway Analysis Using Key Node Genes

Pathways each having two or more key nodes (two or more # Hits in groups) were extracted from the TRANSPATH database (p<0.05).

(3) Study Results (3-1) Significantly Differentially Expressed Variable Gene

Specific significantly differentially expressed variable genes found herein were 181 genes (consisting of 177 overexpressed genes and 4 underexpressed genes), 65 genes (consisting of 19 overexpressed genes and 46 underexpressed genes), and 56 genes (consisting of 56 overexpressed genes and 0 underexpressed gene) in the case of HAM alone, the case of AC alone, and the case of both HAM and AC, respectively.

(3-2) Pathway Characteristics Based on Significantly Differentially Expressed Genes There were 12 significant pathways (p<0.05) in HAM. However, all of them except one involved in TGF-β/SMAD were involved in apoptosis control by caspase. The same ABL1 gene (ABL proto-oncogene 1, non-receptor tyrosine kinase, Gene ID: 25) was involved in all of these 11 pathways (FIG. 13). In FIG. 13, the item "Pathway ID of TRANSPATH database" means the ID of the TRANSPATH database (BIOBASE GmbH) which is a database of signal transduction pathways created through manual judgment (curation) of existing published reports. In FIG. 13, abbreviations of molecular names represent the following:

ABL-1a: c-abl oncogene 1, non-receptor tyrosine kinase isoform a;

ABL-1b: isoform b;

TOPBP1: DNA topoisomerase II binding protein 1;

RAD52:DNA repair protein RAD52 homolog (*S. cerevisiae*);

p73α: tumor protein p73 isoformα;

Ubc9: UBE2I (ubiquitin-conjugating enzyme E2I);

Ran: GTP-binding Ran (ras-related nuclear protein);

Smurf-1: E3 ubiquitin-protein ligase SMURFI; and cIAP-2: BIRC3 (a member of IAP family that inhibit apoptosis by binding TRAF1 and 2).

In FIG. 13, the item "#Hits in group" means the number of genes in the list of genes existing in the pathway. In FIG. 13, the item "Group size" means the total number of genes, proteins, metabolites, and the like existing in the pathway. In FIG. 13, the item "#Hits expected" means the number of genes that may be accidentally included in the gene list. In FIG. 13, the item "P-value" means the value tested by the two-tailed Fisher's exact test regarding independence of row and column factors for a 2×2 contingency table when a gene in the gene list existing in the pathway may or may not be accidentally included. In FIG. 13, significant pathways with P<0.05 are shown as HAM pathology-specific pathways in a descending order of P values.

In the case of AC, two significant pathways including genes of the cellular stress-related MAPK pathway located upstream of caspase were extracted (details omitted). In addition, there was no significant pathway (with two or more hit genes) common to HAM/AC.

(3-3) Upstream Analysis (3-3-1) Search of Transcription Factor Binding Sites

A consensus sequence was constructed from the HAM-specific gene promoter region and the AC-specific gene promoter region and compared with a database of transcription factor binding sites. As a result, 56 transcription factors in HAM and 21 transcription factors in AC were predicted upstream of the differentially expressed gene. Search of the association with HTLV-1 in the database revealed that most of the transcription factors were unknown in terms of the association except those known to be associated with HTLV-1 (such as C/EBP, ATF2 (CREB2), and GATA1,3) in HAM, and those common to HAM and AC were occasionally found (details omitted).

(3-3-2) Key Node Analysis

In key node analysis predicted from the HAM-specific gene group, 23 key node molecules such as CaMKII which is one of CREB phosphorylation kinases, apoptosis-related genes (Fas, Daxx), TGF-βR, Jak1/2, p38MAPK, adapter molecule Crk which is known to be associated with HTLV-1, and an insulin receptor (InsR) were extracted.

In key node analysis of AC, 47 key node molecules including cytokines and receptors such as IFN-α1, IL-4R, IL-10R, and IL-22R and Jak/Tyk kinases such as Jak3 and Tyk were extracted.

(3-3-3) Pathway Analysis Using Key Node Genes

Significant pathways including key node molecules extracted herein were 66 pathways in HAM and 65 pathways in AC. In HAM, pathways related to phosphorylation signals from the insulin receptor and pathways of the Jak-STAT system and p38 MAPK were significant. In AC, in addition to pathways related to phosphorylation signals from the insulin receptor, pathways related to molecules close to the cell membrane such as Jak3, Tyk2, SHP-1, SHP-2, CAS, and CrkL were significant (details omitted).

(4) Discussion

The array data of HAM are reported in Tattermusch S, Skinner J A, Bangham C R. et al. PLoS Pathog. 2012 January; 8(1):e1002480. Systems biology approaches reveal a specific interferon-inducible signature in HTLV-1-associated myelopathy (hereinafter referred to as "references"). The references reported that peripheral leukocytes were characterized by excessive expression of IFN-inducible genes (e.g., STAT1 and 2, TAP1, CXCL10 (IP-10), and IFI35) in HAM, which were similarly observed in monocytes and neutrophils. In addition, Ingenuity (Ingenuity Systems) is used as the de facto standard software for pathway analysis in the references, which does not allow upstream analysis. The Explain (including the TRANSPATH and TRANSFAC databases) used in this Experimental Example allows upstream analysis (Kel A., Voss N., Wingender E., et al. BMC Bioinformatics. 2006, 7(Suppl 2):S13. Beyond microarrays: Finding key transcription factors controlling signal transduction pathways). In addition, the method in this Experimental Example comprising, for example, enriching and examining CD4+ T cells, which are the major source of infection of HTLV-1 other than well as peripheral leukocytes as a whole, differed from those in the references. As a result, the conclusion differed as well.

For pathways with HAM-specific variable genes, caspase-related apoptosis and the upstream stress response-related pathway involving ABL1 are characteristic. The results were considered to be consistent with the fact that caspase is clinically observed in the pathology of the HAM spinal cord.

Meanwhile, in AC, a stress response pathway such as MEKK2 (MAPK kinase 2) upstream of the MAPK signaling pathway is characteristic, suggesting that it is not apoptotic unlike HAM.

Search of transcription factor binding sites as a part of upstream analysis revealed that there are many transcription factors which remain unknown in literature in terms of the association with HTLV-1 in both HAM and AC. It was therefore considered that the pathological signal transduction pathway of HTLV-1 has not been sufficiently studied.

Key node analysis of HAM revealed that the transcription factor CREB was included in the connecting gene within 4 nodes from the key node of HAM/AC, while NF-κB important for ATL signal transduction was not included, which probably reflect that HAM is deeply related to CREB, which is involved in inflammation and the JAK-STAT system downstream of cytokine, and ATL is deeply related to NF-κB associated with cell proliferation during signal transduction. The same also applied to specific pathways of specific variable genes.

Signals from the insulin receptor were extracted from both HAM and AC in the upstream pathway using key node molecules. In general, those signals are considered to provide energy in the considerably upstream of phosphorylation signals.

In summary, in this Experimental Example, among 177 genes extracted as HAM pathology-specific responsible genes in peripheral blood CD4+ T cells, ABL1 was extracted as a HAM pathology-specific pathway. In upstream analysis, there was no convergence to a small number of genes, and no other genes were found to be promising genes for gene target therapy or molecular target therapy for HAM.

ABL1 is also a gene related to an apoptotic pathway involving caspase as in the case of the HAM spinal cord and this is consistent with conventional pathological findings in the HAM spinal cord. Therefore, ABL inhibitors targeting ABL1 inhibition could be available for gene target therapy or molecular target therapy for HAM.

(5) Conclusion

ABL1 tyrosine kinase was identified as a promising target for HAM treatment from HAM pathology-specific responsible genes or pathways extracted using array data of peripheral blood CD4+ T cells in HAM.

Example 2

In this Example, a novel quantitative determination method, PMA (propidium monoazide)-HTLV-1 viability PCR, by which the proviral load (PVL) of HTLV-1 only in live cells can be quantitatively determined, was developed. This technique was used to examine whether ABL1 inhibitors have an effect of reducing the proviral load of HTLV-1 in living cells. In the usual PVL measurement method, PVL of dead cells and PVL of living cells cannot be distinguished from each other for measurement, meaning that PVL is collectively measured for both cells.

PMA-HTLV-1 viability PCR, which is a novel quantitative determination method, will be described in detail in Experimental Example 2 below. The method is based on conventionally known PMA viability PCR (Nocker A. et al. J Microbiol Methods 2006. 67: 310-320).

(1) Assay of ABL1 Inhibitors by PMA-HTLV-1 Viability PCR
(1-1) Preparation of Experimentation
(1-1-1) Subjects/Cells PBMCs from 16 HAM cases frozen and preserved in liquid nitrogen were used.

(1-1-2) PMA Treatment/Photo-Crosslinking

The method of PMA treatment is similar to PMA-HTLV-1 viability PCR described in detail later. A PMA stock solution (20 mM, frozen and preserved at −20° C. under light protection) was added to cell samples to yield a final concentration of 50 μM, and the tubes were incubated in a dark place (wrapped in aluminum foil) at room temperature for 5 minutes (each tube was sometimes flicked by fingers for mixing).

A photo-crosslinker and a halogen lamp were always used to perform photo-crosslinking using a household 100-V AC power source. The cell specimen volume was adjusted by appropriately adding PBS to 200 μL and irradiation was carried out for 5 minutes at a position 20 cm away from the halogen lamp in the dark. Air-cooling was performed during irradiation such that the sample temperature did not rise above 37° C. Each sample tube was sometimes flicked by fingers for mixing (1-1-3) Drugs (Imatinib and Nilotinib)

Based on the ABL1 50% inhibitory concentration (IC50) in the package inserts of imatinib and nilotinib and the Cmax concentration data from in vivo dynamics examination data, and the molecular weights, 600 nM imatinib and 30 nM nilotinib were examined in terms of IC50, and 5 μM imatinib and 3 μM nilotinib were examined in terms of Cmax.

(1-2) Experimental Protocol
(1-2-1) Cell Specimen Washing and Cell Concentration Count Frozen PBMC specimens were thawed in a water bath at 37° C. and washed twice with PBS at 300×g, and then, the pellet was suspended in 1 mL of PBS and placed on ice. The cell concentration was counted by the trypan blue exclusion method using a hemocytometer.

(1-2-2) Treatment of Drug-Untreated DNA Samples (T=0 h)

Approximately $5 \times 10^5$ to $1 \times 10^6$ cells were collected in two Eppendorf tubes and the solution volume was adjusted to 200 μL by adding PBS if appropriate. One of the tubes was subjected to PMA treatment and photo-crosslinking, and the other tube was not treated in the same manner. DNA was extracted from both tubes using DNeasy Blood & Tissue Kits (QIAGEN).

PMA-untreated DNA was named "Sample No-D(Drug)-P-" and PMA-treated DNA was named "Sample No-D+P+."

(1-2-3) Treatment with Drugs (Imatinib and Nilotinib)

To the remaining liquid of the cell suspension of each cell specimen, approximately 7.5 mL of cell medium RPMI1640 (supplemented with 10% of fetal calf serum and 1% of penicillin-streptomycn) was added to adjust the total volume to 8.0 mL+α. Each mixture was plated in a volume of approximately 2000 μL on a 6-well polystyrene plate such that 4 wells were used per cell specimen. Imatinib and nilotinib were added to yield a final concentration of 600 nM or 5 μM and a final concentration of 30 nM or 3 μM, respectively, per cell specimen.

(1-2-4) Incubation

After adding the drug, each mixture was gently shaken on a shaker and incubation was started at 37° C. in a 5% $CO_2$ incubator.

(1-2-5) Harvesting, PMA Treatment, and DNA Extraction at T=6 h

At T=6 h, about a half volume of the cell suspension of each well was harvested, collected in an Eppendorf tube, and centrifuged at 3,500 rpm×10 min. The supernatant was discarded, and the pellet was resuspended with 1 mL of PBS. Centrifugation was performed again at 3,500 rpm×10 min, and the supernatant was discarded, followed by washing. PBS was added to yield a volume of 200 μL, and all specimens were subjected to PMA treatment and photo-crosslinking. Subsequently, the specimens were washed with PBS again, and DNA was extracted with DNeasy Blood & Tissue Kits (QIAGEN).

DNA samples were named, for example, "Sample No-imatinib600 nM-6 h."

(1-2-6) Harvesting, PMA Treatment, and DNA Extraction at T=12 h

The procedures were performed as in the case of T=6 h described in (1-2-5) above. DNA samples were named, for example, "Sample No-Imatinib600 nM-12 h."

(1-2-7) DNA Concentration Measurement and Working Solution Preparation

The DNA concentration was measured by ND-1000 (Thermo Fisher Scientific), and DNA was prepared in an amount (10 ng/µL×triplicate or more) sufficient for real-time PCR to be performed in triplicate. DNA was frozen and preserved at −20° C. until use.

(1-2-8) Measurement by Real-Time PCR Using TaqMan Probes (Triplicate)

According to the protocol (for the PCR system of 25 µL in total) of TaqMan Universal Master Mix II (#4440044, Thermo Fisher Scientific), 20 µM forward and reverse primers, 8 µM TaqMan probes, 2× Universal Master Mix II, and D2 W were mixed. The mixture was pipetted in a volume of 25 µL into each of triplicate wells of a MicroAmp Fast 96-well Reaction Plate (0.1 mL) (REF 4346907, Applied Biosystems) provided with MicroAmp Optical Adhesive Film (P/N 4311971, Applied Biosystems).

A standard dilution series for standard curve creation was prepared from the following five points for pX: NTC (No Template Control); 2 copies/µL (10 copies at 5 µL); 20 copies/µL (100 copies at 5 µL); 200 copies/µL (1000 copies at 5 µL); and 2000 µL (10000 copies at 5 µL).

The thermal cycle program was carried out using the StepOne Plus real-time PCR system (Applied Biosystems) and StepOne software ver. 2.3 with 1 cycle in a holding stage at 50° C.×2 minutes and 95° C.×10 minutes and 45 cycles of amplification at 95° C.×15 seconds and 60° C.×1 minute.

(1-2-9) Method for Calculating PMA-HTLV-1 Viability PCR Indexes

Index of the Cτ extension effect by ABL1 inhibitor treatment:

$$\Delta C\tau_{Drug} = C\tau_{D-P+} - C\tau_{D+P+}$$ [Formula 3]

Index of the effect of reducing the HTLV-1 viral load by ABL1 inhibitor treatment:

$$pX \text{ decrease rate in live cells } (\%) = \left(1 - 10^{\frac{-\Delta C\tau_{Drug}}{slope}}\right) \times 100$$ [Formula 4]

The above indexes were calculated from DNA samples at T=0 in the D−P+ sample group and DNA samples (D+P+ group) from cells allocated by drugs and concentrations at T=6 h and T=12 h.

(1-2-10) Test

The calculation results were summarized by drugs and concentrations and the above indexes were tested by the t-test (Paired t-test) with a correspondence between concentrations in a time series (T=0 h, 6 h, and 12 h), concentrations by drugs, or drugs by concentrations (IC50 and Cmax). All samples were examined at N=16.

(2) Assay Results (2-1) Assay Results of ABL1 Inhibitors by PMA-HTLV-1 Viability PCR The index of the effect of Cτ extension by ABL1 inhibitor treatment ($\Delta C\tau_{Drug}$) and the pX decrease rate in live cells (%) were calculated, and the calculation results were summarized in Table 3.

TABLE 3

| | Drug treatment | | | | | | | | | | | |
|---|---|---|---|---|---|---|---|---|---|---|---|---|
| | Imatinib 600 nM | | | Imatinib 5 µM | | | Nilotinib 30 nM | | | Nilotinib 3 µM | | |
| | Harvesting time | | | | | | | | | | | |
| | 0 h | 6 h | 12 h | 0 h | 6 h | 12 h | 0 h | 6 h | 12 h | 0 h | 6 h | 12 h |
| ΔCτ Drug | | | | | | | | | | | | |
| Mean | 0 | −1.30 | −1.96 | 0 | −0.99 | −1.49 | 0 | −2.03 | −2.63 | 0 | −0.86 | −1.46 |
| Standard deviation (SD) | 0 | 0.97 | 1.22 | 0 | 0.66 | 0.94 | 0 | 0.85 | 0.95 | 0 | 0.58 | 1.05 |
| Standard error (SE) | 0 | 0.24 | 0.30 | 0 | 0.16 | 0.24 | 0 | 0.21 | 0.24 | 0 | 0.15 | 0.26 |
| pX decrease rate in live cells (%) | | | | | | | | | | | | |
| Mean | 0 | 50.35 | 66.37 | 0 | 43.37 | 44.99 | 0 | 69.51 | 78.00 | 0 | 53.82 | 36.19 |
| Standard deviation (SD) | 0 | 22.38 | 17.54 | 0 | 19.31 | 39.71 | 0 | 13.70 | 10.39 | 0 | 15.61 | 37.20 |
| Standard error (SE) | 0 | 5.60 | 4.38 | 0 | 4.83 | 9.93 | 0 | 3.43 | 2.60 | 0 | 3.90 | 9.30 |

Figure 14:
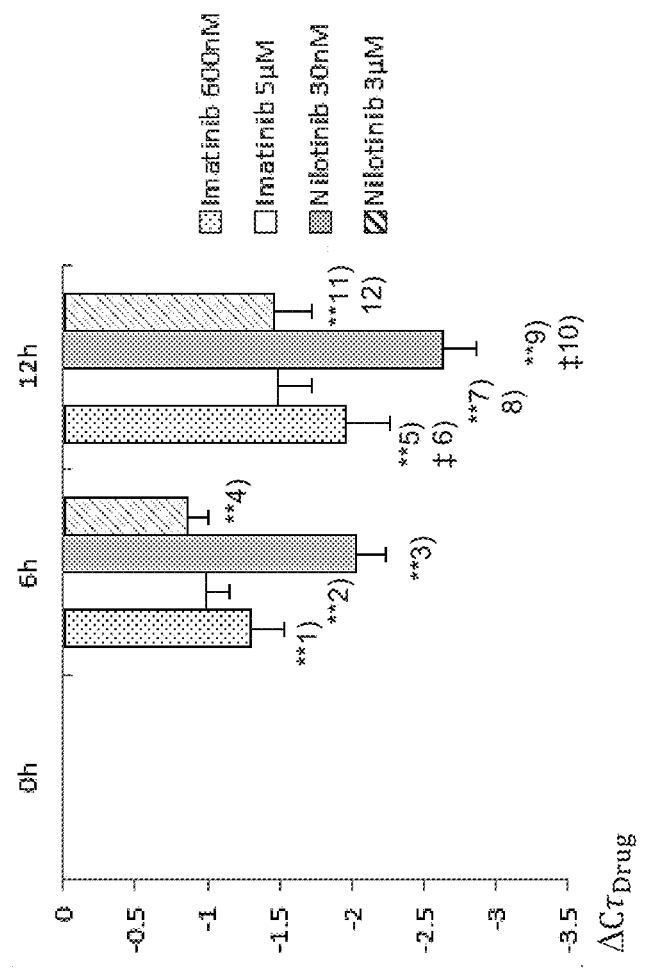
FIG. 14 is a characteristic chart indicating the relationship between $\Delta C\tau_{Drug}$ and ABL1 inhibitor treatment.

(2-2) Examination of ABL1 Inhibitors by $\Delta C\tau_{Drug}$ (2-2-1) Time-Series Examination (FIG. 14)

FIG. 14 depicts the results. In FIG. 14, the difference from T=0 h was considered significant at *P<0.05, **P<0.01, and regarding T=12 h, the difference from 6 h was also considered significant at † P<0.05, ‡P<0.01. The numbers following the symbols *, **, t, †, ‡, which indicate significance, are the following significance levels: 1) 7.88E-05; 2) 2.01E-07; 3) 2.56E-12; 4) 6.30E-10; 5) 1.71E-10; 6) 0.0027; 7) 0.0014; 8) 0.85; 9) 8.17E-15; 10) 0.0071; 11) 0.0014; 12) 0.069. Numbers not preceded by symbols are not significant (N=16, Paired t-test).

As depicted in FIG. 14, as compared with T=0, the Cτ extension effect was significant at T=6 h and T=12 h with a significance level of 1% or less for either imatinib (600 nM or 5 µM) or nilotinib (30 nM or 3 µM). At T=12 h, as compared with T=6 h, the Cτ extension effect was significantly observed at low concentrations (IC50) of 600 nM for imatinib and 30 nM for nilotinib, while there was no significance at high concentrations (Cmax) of both drugs.

Figure 15:
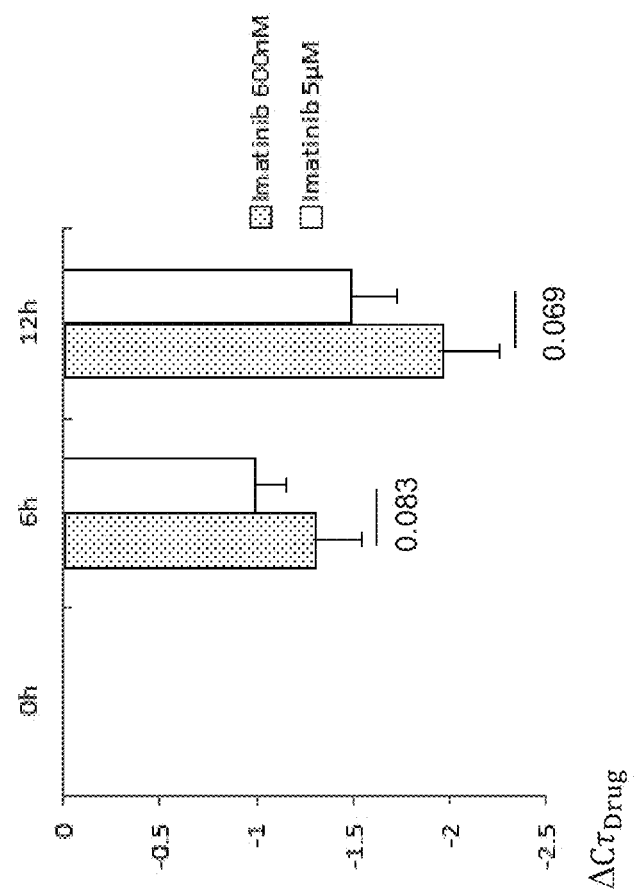
FIG. 15 is a characteristic chart indicating the relationship between $\Delta C\tau_{Drug}$ and the imatinib concentration.
Figure 16:
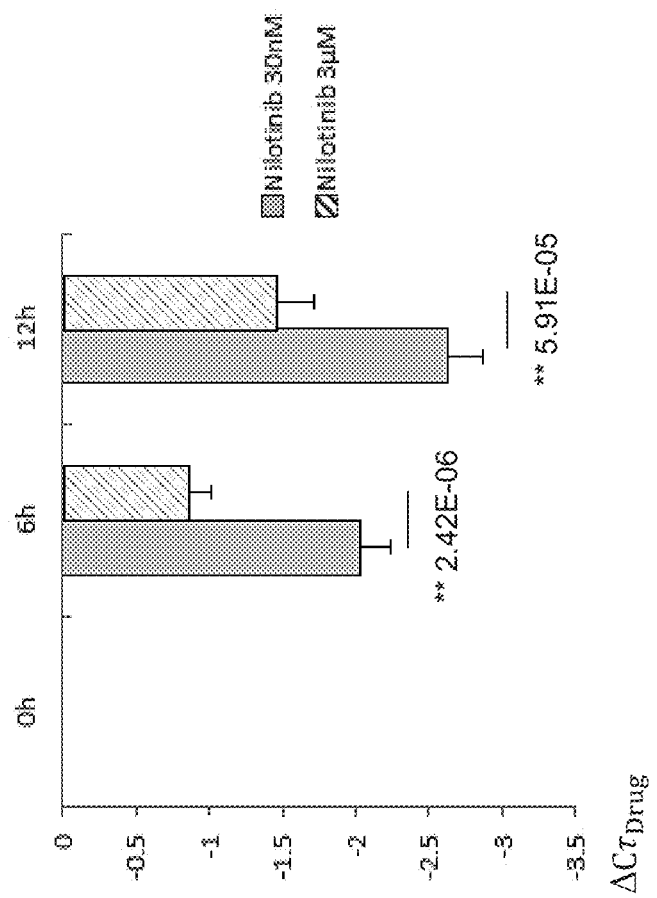
FIG. 16 is a characteristic chart indicating the relationship between $\Delta C\tau_{Drug}$ and the nilotinib concentration.

(2-2-2) Comparison Between Concentrations (FIGS. 15 and 16)

FIG. 15 depicts the results obtained when imatinib was used. As depicted in FIG. 15, although there was no significant difference for 600 nM imatinib vs 5 µM imatinib, the Cτ extension effect at the low concentration (600 nM) at T=6 h and T=12 h tended to be relatively greater than the effect at the high concentration (5 µM).

FIG. 16 depicts the results obtained when nilotinib was used. As depicted in FIG. 16, upon comparison of 30 nM nilotinib vs 3 µM nilotinib, the Cτ extension effect at the low concentration (30 nM) at T=6 h and T=12 h was significantly greater than that at the high concentration (3 μM) with a significance level of 1% or less.

Figure 17:
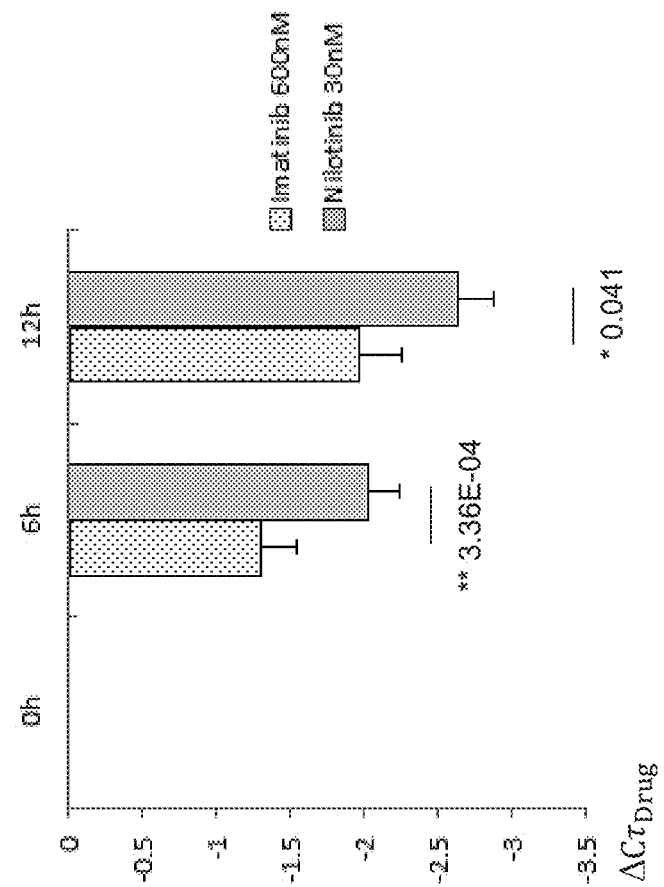
FIG. 17 is a characteristic chart indicating the relationship between $\Delta C\tau_{Drug}$ and each of imatinib and nilotinib at IC50.
Figure 18:
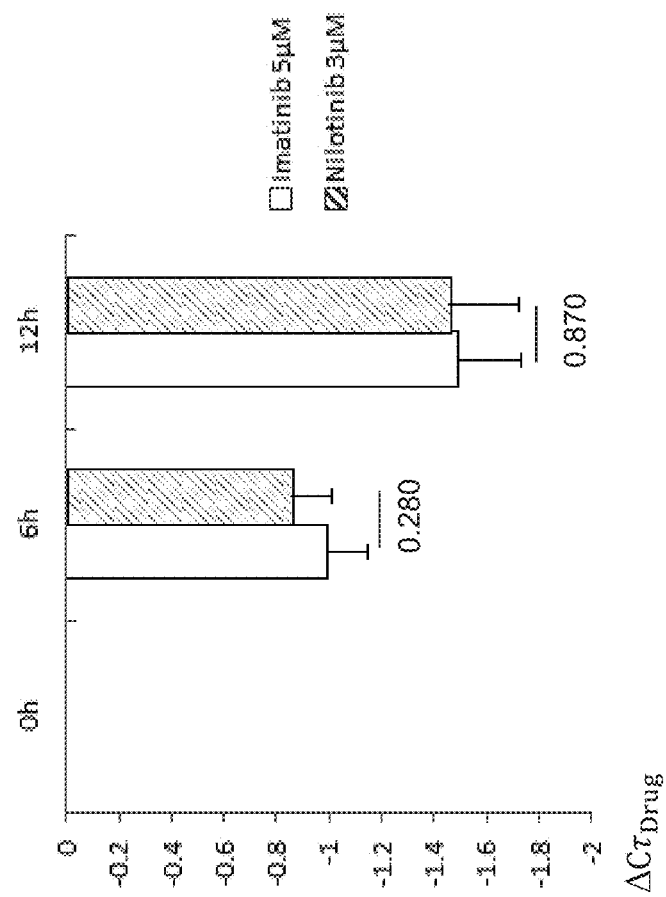
FIG. 18 is a characteristic chart indicating the relationship between $\Delta C\tau_{Drug}$ and each of imatinib and nilotinib at Cmax.

(2-2-3) Comparison Between Drugs (FIGS. 17 and 18)

FIG. 17 depicts the results of comparison at IC50 (600 nM imatinib vs 30 nM nilotinib). As depicted in FIG. 17, the Cτ extension effect at T=6 h and T=12 h for 30 nM nilotinib was significantly greater than that for 600 nM imatinib with a significance level of 1% or less.

FIG. 18 depicts the results of comparison of high concentration Cmax (5 μM imatinib vs 31 μM nilotinib). As depicted in FIG. 18, there was no significant difference at T=6 h and T=12 h.

(2-3) Examination of ABL1 Inhibitors Based on the pX Decrease Rate in Live Cells (%)

Figure 19:
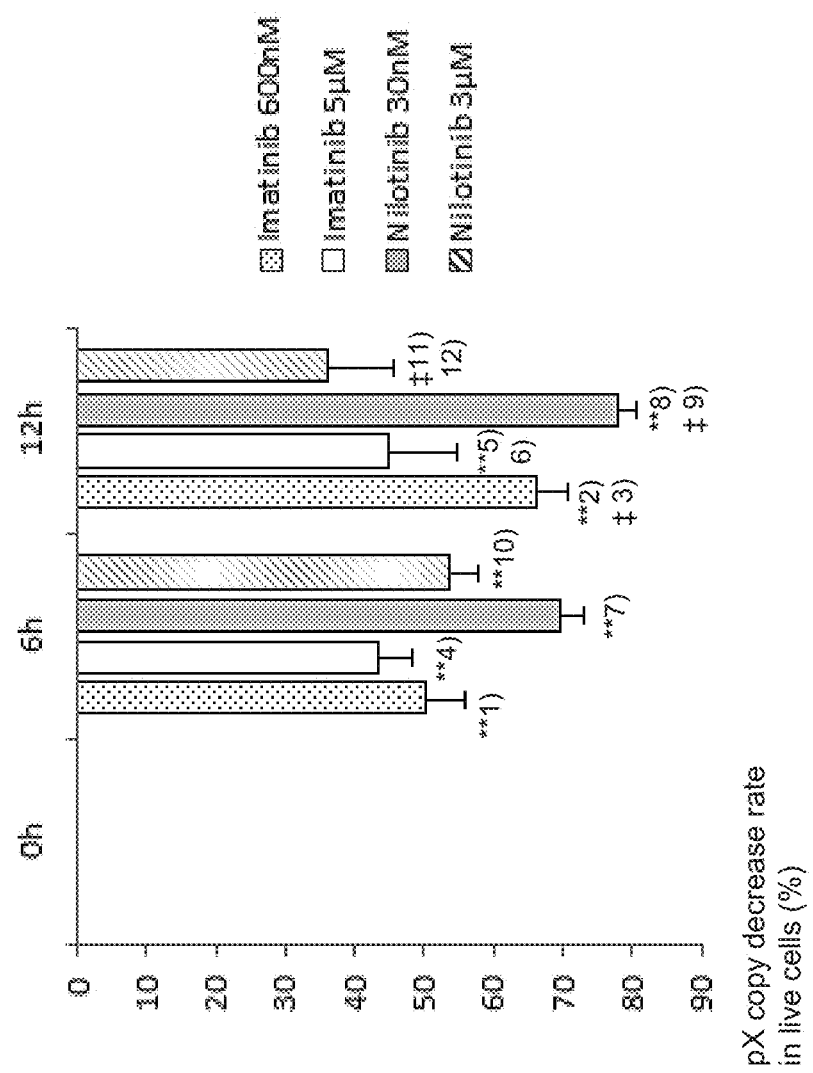
FIG. 19 is a characteristic chart indicating the relationship between the pX decrease rate in live cells and ABL1 inhibitor treatment.

(2-3-1) Time-Series Examination (FIG. 19)

FIG. 19 depicts the results. In FIG. 19, the difference from T=0 h was considered significant at *P<0.05, **P<0.01, and regarding T=12 h, the difference from 6 h was also considered significant at † P<0.05, ‡P<0.01. The numbers following the symbols *, **, †, ‡, which indicate significance, are the following significance levels: 1) 1.97E-07; 2) 1.71E-10; 3) 0.0027; 4) 2.01E-07; 5) 0.0014; 6) 0.846; 7) 2.56E-12; 8) 8.17E-15; 9) 0.0071; 10) 6.30E-10; 11) 0.0014; 12) 0.069. Numbers not preceded by symbols are not significant (N=16, Paired t-test).

As depicted in FIG. 19, as compared with T=0, the effect of reducing pX copies in live cells was significant at T=6 h and T=12 h with a significance level of 1% or less for either imatinib (600 nM or 5 μM) or nilotinib (30 nM or 3 μM). At T=12 h, as compared with T=6 h, the effect of reducing pX copies in live cells was significantly observed at low concentrations (IC50) of 600 nM for imatinib and 30 nM for nilotinib, while there was no significance at high concentrations (Cmax) of both drugs.

The pX decrease rates in live cells at the low concentration (IC50) at T=6 h and 12 h were 50.35% and 66.37%, respectively, for 600 nM imatinib, and 69.51% and 78.00%, respectively, for 30 nM nilotinib. Thus, it was revealed that both drugs can remarkably reduce the proviral load.

Figure 20:
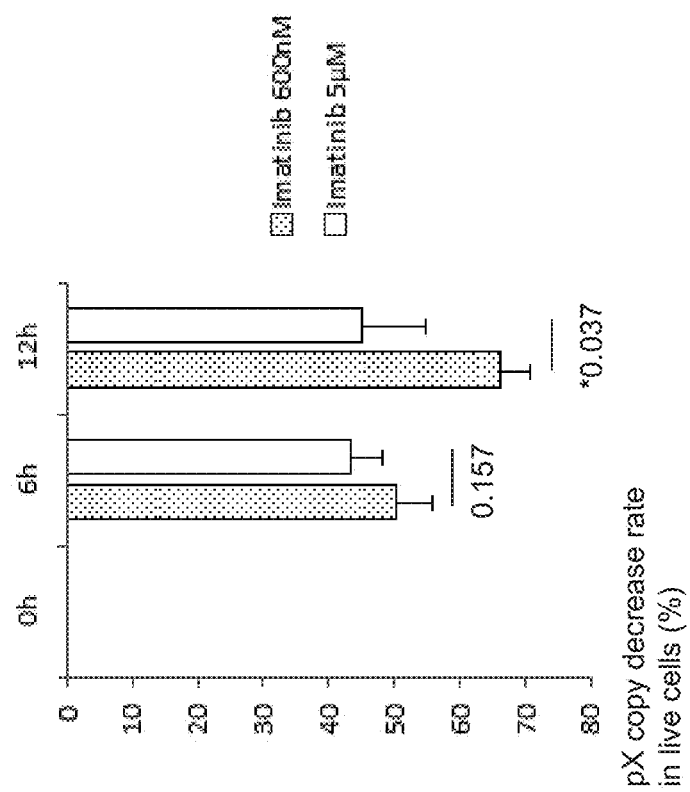
FIG. 20 is a characteristic chart indicating the relationship between the pX decrease rate in live cells and the imatinib concentration.
Figure 21:
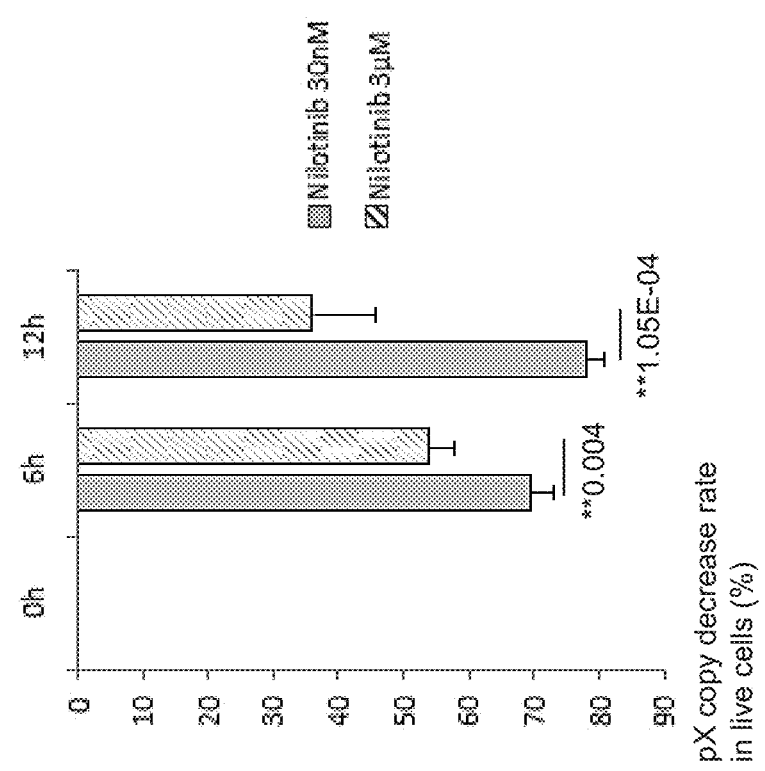
FIG. 21 is a characteristic chart indicating the relationship between the pX decrease rate in live cells and the nilotinib concentration.

(2-3-2) Comparison Between Concentrations (FIGS. 20 and 21)

FIG. 20 depicts the results obtained when imatinib was used. As depicted in FIG. 20, although there was no significant difference at T=6 h for 600 nM imatinib vs 5 μM imatinib, the pX decrease rate in live cells at the low concentration (600 nM) tended to be relatively greater than that at the high concentration (5 μM). At T=12 h, the pX decrease rate in live cells at the low concentration (600 nM) was significantly greater than that at the high concentration (5 μM).

FIG. 21 depicts the results obtained when nilotinib was used. As depicted in FIG. 20, upon comparison of 30 nM nilotinib vs 3 μM nilotinib, the pX decrease rate in live cells at the low concentration (30 nM) at either T=6 h or T=12 h was significantly greater than that at the high concentration (3 μM) with a significance level of 1% or less.

Figure 22:
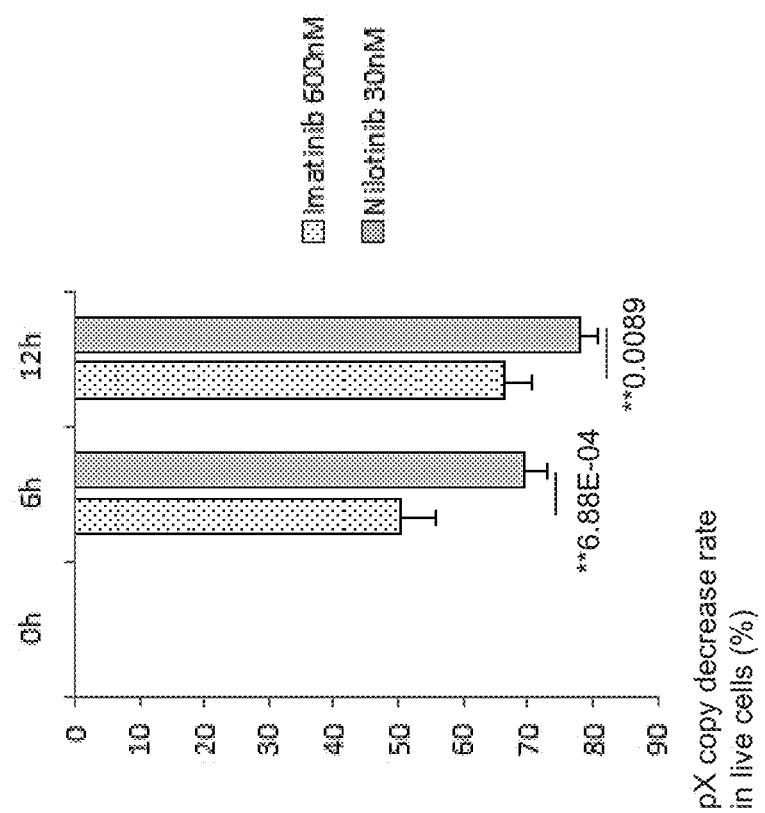
FIG. 22 is a characteristic chart indicating the relationship between the pX decrease rate in live cells and each of imatinib and nilotinib at IC50.
Figure 23:
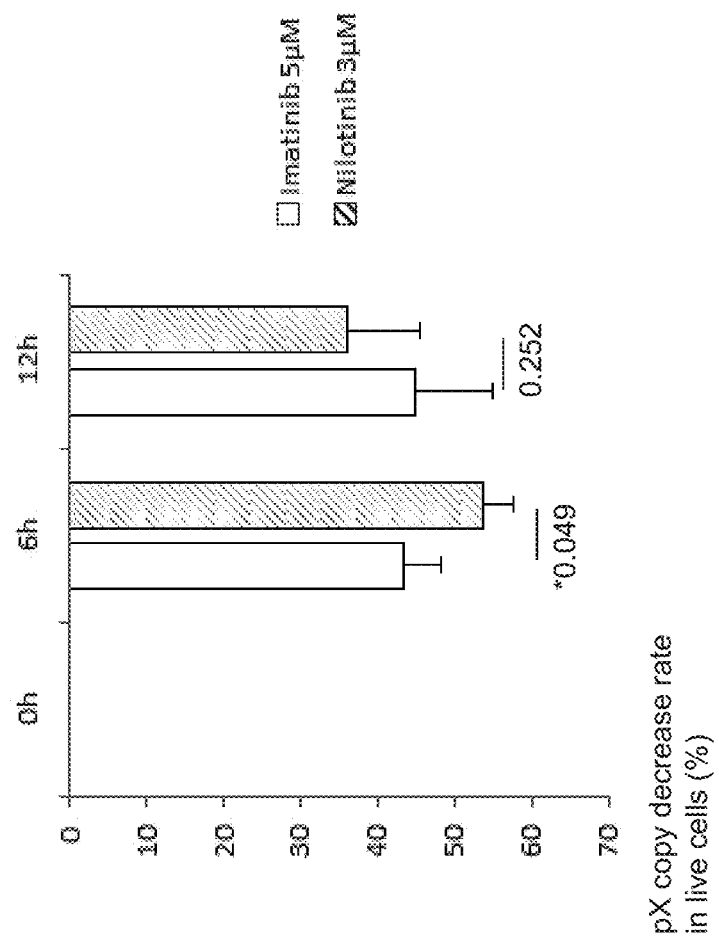
FIG. 23 is a characteristic chart indicating the relationship between the pX decrease rate in live cells and each of imatinib and nilotinib at Cmax.

(2-3-3) Comparison Between Drugs (FIGS. 22 and 23)

FIG. 22 depicts the results of comparison at IC50 (600 nM imatinib vs 30 nM nilotinib). As depicted in FIG. 22, the pX decrease rate in live cells at either T=6 h or T=12 h for 30 nM nilotinib was significantly greater than that for 600 nM imatinib with a significance level of 1% or less.

FIG. 23 depicts the results of comparison of high concentration Cmax (5 μM imatinib vs 3 μM nilotinib). As depicted in FIG. 23, the pX decrease rate in live cells for 3 μM nilotinib was significantly greater than that for 5 μM imatinib at T=6H. There was no significant difference at T=12 h.

(3) Discussion

As described in (2) above, by conducting assay of ABL1 inhibitors by PMA-HTLV-1 viability PCR, it was possible to reveal that in addition to $\Delta C\tau_{Drug}$ which is an index of the Cτ extension effect and the pX decrease rate in live cells (%), the HTLV-1 proviral load in live cells treated with ABL1 inhibitors decreases as compared with drug-untreated cells.

It was found that these effects such as the reduction effect of ABL1 inhibitors are significantly maintained also in a time series of T=6 h and 12 h. In Example 1. FIG. 3 depicts time-dependent changes in the cell concentration during in vitro culture of HAM- and NC-derived CD4+ T cells and non-CD4 PBMCs in a drug-untreated state. As depicted in the figure, in the in vitro state, that is to say, the ex vivo state free of neutralizing antibodies, HAM-derived CD4+ T cells spontaneously proliferate at T=24 h to 48 h (spontaneous proliferation). In other words, in consideration of the fact that the proviral load tends to increase, it is expected that prolongation of the virus reduction effect for a relatively long period of time will be highly advantageous in HAM treatment.

In addition, the effects were more significant for nilotinib than imatinib at the same concentration (IC50). This is considered to be consistent with the fact that nilotinib is a more specific second-generation drug.

The results obtained for the same drug indicated that the low concentration (IC50) has a significantly higher virus reduction effect in living cells than the high concentration (Cmax) for both imatinib and nilotinib. For example, ABL1 tyrosine kinase was extracted as a HAM pathology-specific responsible gene and also as a gene involved in the HAM pathology-specific pathway, ABL1 was found as a gene involved in apoptosis/survival of CD4+ T cells in HAM, and ABL1 is a multifunctional molecule involved in various events in cells. In consideration of these facts, as suggested by the above experimental results, it is understood that low-concentration ABL1 inhibitor treatment strongly drives cells in the direction of cell death.

Macrophages immediately recognize and phagocytize CD4+ T cells whose cell membranes are broken in vivo while there are few macrophages in an in vitro culture system. In view of this, in a case in which ABL1 inhibitors are administered in vivo, it is expected that the clinical test results, which will directly reflect the effect of reducing the viral load in live cells in vitro as described in this Example, can be obtained.

As already mentioned, ABL1 inhibitors are clinically applied molecular targeted drug for chronic myelogenous leukemia (CML). It is expected that new indications will be added to HAM for the purpose of reducing the HTLV-1 proviral load.

Experimental Example 2

In Experimental Example 2. PMA-HTLV-1 viability PCR, which is a novel method for quantitative determination of PVL only in live cells, will be explained.

[PMA Viability PCR]

First, an outline of the basic PMA viability PCR will be explained. PMA (propidium monoazide) is a membrane impermeable, nucleic acid (DNA/RNA)-binding fluorescent dye, in which the azide group has photoreactivity. PMA Viability PCR was invented by Nocker et al. in 2006 for the purpose of determining whether microorganisms in samples such as environmental specimens, foods, and the like are alive (Nocker A. et al. J Microbiol Methods 2006. 67: 310-320).

PMA enters dying cells or dead cells (collectively referred to as "dead cells"), in which membrane integrity (asymmetry) has been lost, and preferentially binds to double-stranded DNA. However, PMA does not penetrate live cells having membrane integrity.

PMA bound to double-stranded DNA irreversibly binds to DNA strands by photo-crosslinking with irradiation at an absorption wavelength of 464 nm (approximately 470 nm). Meanwhile, photolysis of unbound PMA occurs. When quantitative PCR (qPCR) is performed with extracted DNA as a template, PCR using DNA bound by PMA as a template is inhibited, and therefore, PCR proceeds using only DNA derived from live cells, to which PMA is not bound, as a template. As described above, when DNA serving as a template contains PMA-bound DNA, the number of cycles (Cτ value) reaching the threshold value in quantitative PCR is increased (expanded). Therefore, there are many DNAs not bound by PMA when there are many viable cells (live cells), which facilitates PCR, thereby decreasing the Cτ value, and if there are fewer viable cells (live cells), increasing (expanding) the Cτ value.

As an index for examining the PCR inhibitory effect of PMA, the original paper of Nocker et al. (Nocker A. et al. J Microbiol Methods 2006. 67: 310-320) describes that a value obtained by subtracting Cτ of a PMA-treated specimen from Cτ of the PMA-untreated specimen of the same specimen (resulting in a negative value) is displayed downward as ΔCτ and used (the following formula).

$$\Delta C\tau = C\tau w/o\ PMA - C\tau\ with\ PMA \quad [\text{Formula 5}]$$

Cτw/o PMA: Cτ value measured by PCR of DNA extracted after treatment without PMA Cτ with PMA: Cτ value measured by PCR of DNA after PMA treatment of the same cell sample

[PMA-HTLV-1 Viability PCR]

In this Experimental Example, a novel method for quantitatively determining PVL only in live cells (referred to as "PMA-HTLV-1 viability PCR") is proposed. After expanding the protocol and calculation theory of PMA viability PCR, PMA-HTLV-1 viability PCR is introduced.

(1) Expansion of the Protocol and Calculation Theory of PMA Viability PCR (1-1) Expansion of the Protocol of PMA Viability PCR According to the protocol of PMA viability PCR, unlike the usual absolute method of real-time PCR, a standard curve is not created using a standard product dilution series of a target nucleic acid. In this Experimental Example, a case in which the protocol is carried out according to the absolute method of real-time PCR using a standard product of a target nucleic acid and its dilution series, a primer set for the target nucleic acid, and TaqMan probes is considered.

Cells to be measured are divided into two groups, which are designated as a group to be treated without PMA (w/o (without) PMA) and a group to be treated with PMA (with PMA). DNA is extracted. The standard of the target nucleic acid and the target nucleic acid copy number in a DNA sample to be measured are determined in triplicate in accordance with the protocol based on the absolute method of real-time PCR.

(1-2) Expansion of the Calculation Theory of PMA Viability PCR

In real-time PCR, the fluorescence intensity indicating the amplification product is usually regarded as a sample blank at the noise level from the 1st to 10th (maximum) cycles, and the standard deviation (SD) is calculated to set 10SD as a threshold. The cycle number that exceeds the threshold for the first time is set as a cycle threshold (Cτ) value. The amount of DNA applied in accordance with the real-time PCR protocol is constant. However, if the amount of the target initial template DNA at the start of PCR is large, the Cτ value becomes small, and if it is small, the Cτ value becomes large.

Figure 24:
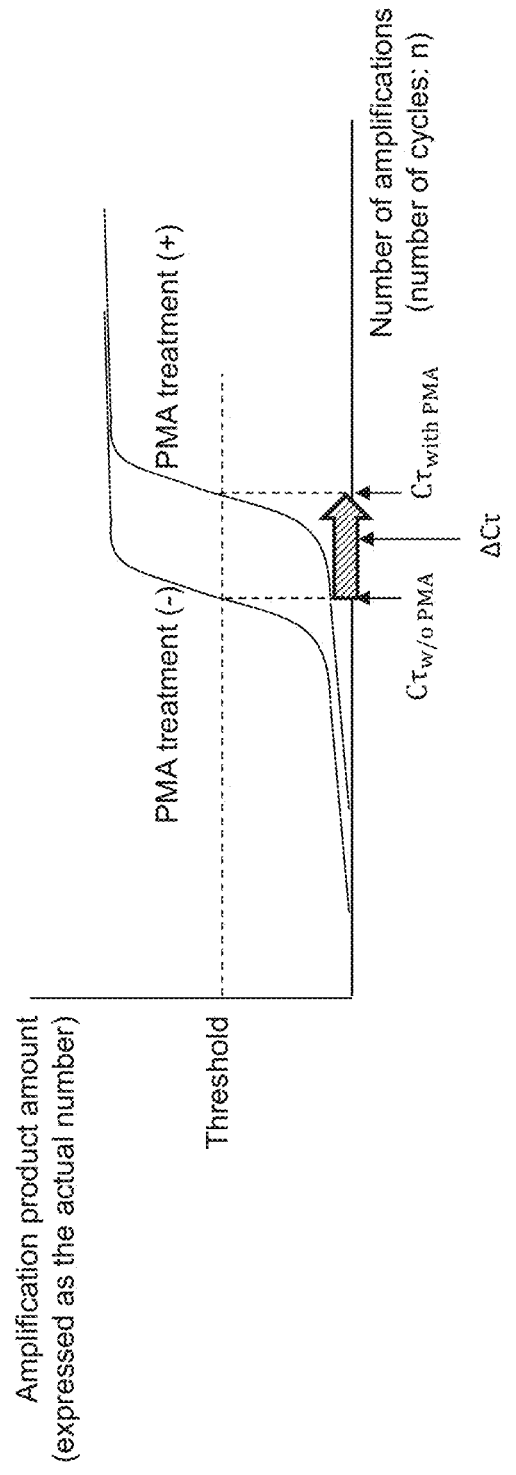
FIG. 24 is a characteristic chart indicating the relationship between the number of amplifications (number of cycles) and the amplification product amount (actual number) in PMA viability PCR.
Figure 25:
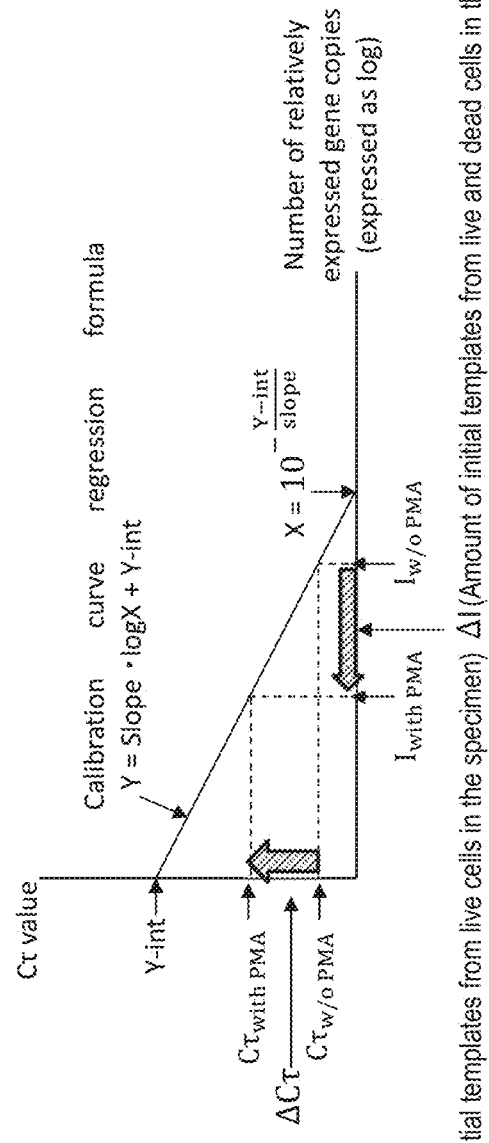
FIG. 25 is a characteristic chart indicating the relationship between Cτ and the number of relatively expressed gene copies (expressed as log) in PMA viability PCR.
Figure 26:
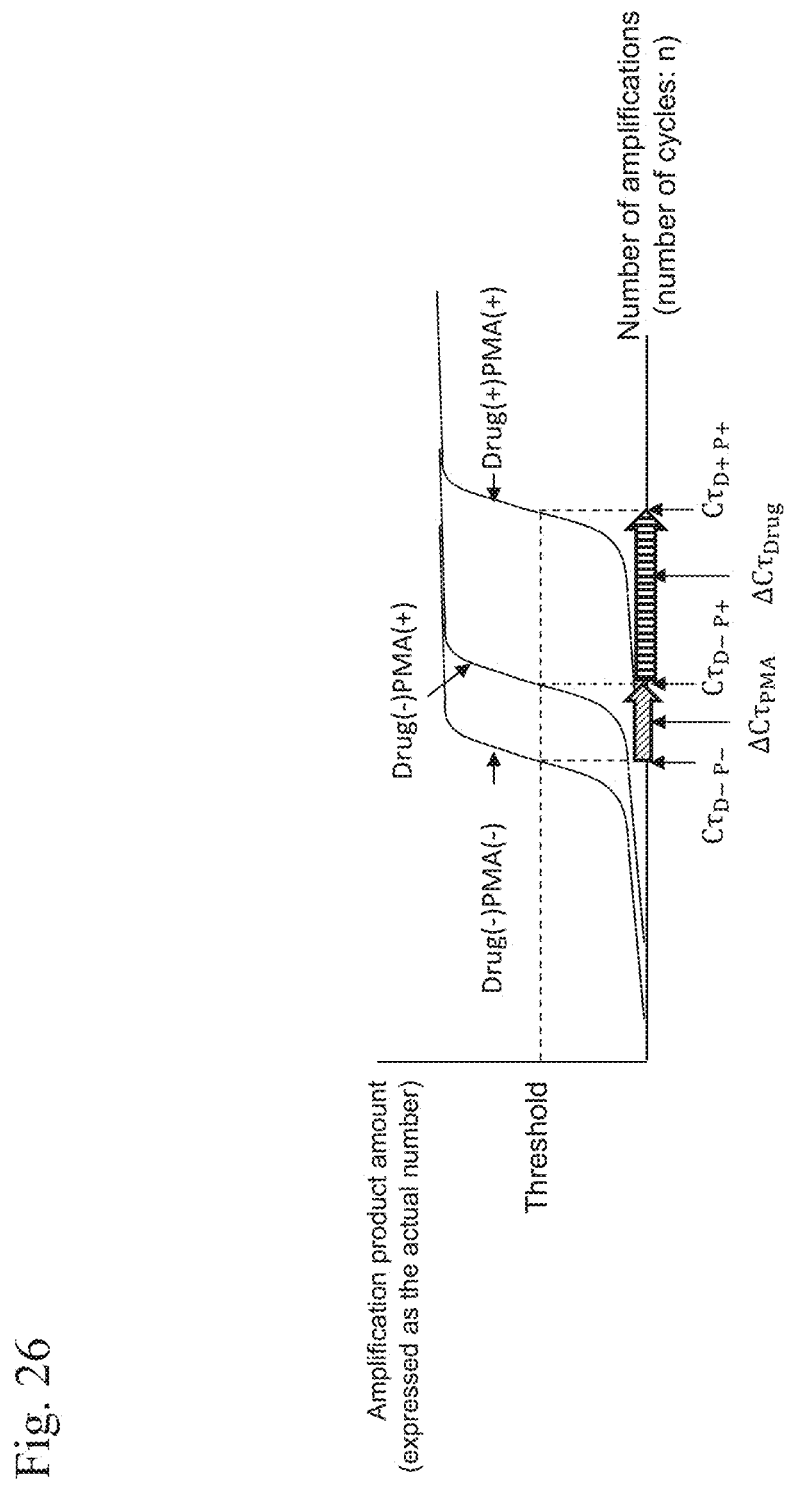
FIG. 26 is a characteristic chart indicating the relationship between the number of amplifications (number of cycles) and the amplification product amount (actual number) in assay of drugs cytotoxic to HTLV-1-infected cells by PMA-HTLV-1 viability PCR.

In view of these relationships and the presence or absence of PMA treatment of cell specimens, FIGS. 24 and 25 depict plots of the number of amplifications—the amplification product amount (actual number) in PCR and plots of Cτ—the number of relatively expressed gene copies (expressed as log).

(1-2-1) the Number of Amplifications (Number of Cycles) and the Amplification Product Amount (Actual Number) in PMA Viability PCR (FIG. 24)

The original paper on PMA viability PCR of Nocker A. et al. (Nocker A. et al. J Microbiol Methods 2006. 67: 310-320) describes that a value obtained by subtracting Cτ of a PMA-treated specimen from Cτ of the same specimen before PMA treatment (a negative value), which is an index for examining the PCR inhibitory effect of PMA, is displayed in a downward graph as ΔCτ and used.

Here, it is attempted to further display ΔCτ on plots of the number of amplifications (number of cycles)–the amplification product amount (actual number) in real-time PCR, which can be displayed as depicted in FIG. 24. In PMA treatment (−), the Cτ value is small while in PMA treatment (+), the amplified product amount curve rises only from live cell DNA and the Cτ value is delayed (increased). Accordingly, ΔCτ, which depends on the number of dead cells, becomes a negative value obtained by subtracting the larger Cτ with the PMA value from the smaller PMA treatment (−) Cτ w/o PMA value.

(1-2-2) Plots of Cτ—the Number of Relatively Expressed Gene Copies (Expressed as Log) in PMA Viability PCR (FIG. 25)

Regarding ΔCτ in FIG. 24, a standard curve (calibration curve regression formula) was obtained by carrying out the absolute method using a standard sample of a target nucleic acid sequence and the corresponding TAQMAN probe at the same time with PMA viability PCR. By using this standard curve, ΔCτ can be plotted on the Y axis (Cτ) as depicted in FIG. 25.

Further, the number of copies of the initial template applied upon PCR is designated to correspond to the following on the X axis of the number of relatively expressed gene copies (expressed as log).

Iw/o PMA: Initial template amount when the Cτ w/o PMA value was obtained by PCR with a PMA treatment (−) sample (number of copies) (expressed as log) Iwith PMA: Initial template amount when the Cτ with PMA value was obtained by PCR with a PMA treatment (+) sample (number of copies) (expressed as log)

In this case, as with ΔCτ, it is possible to newly define and depict a decrease in the initial template amount (number of copies) as a negative value: ΔI=Iw/o PMA−Iwith PMA.

It is also possible to calculate ΔI using the following formula calculated from the standard curve.

$$I_{w/o\ PMA} = 10^{\frac{C\tau_{with\ PMA} - Y\text{-}int}{slope}}, \quad [\text{Formula 6}]$$

-continued $$I_{with\ PMA} = 10^{\frac{Ct_{w/o\ PMA}-Y-int}{slope}}$$

(2) Novel Method for Quantitatively Determining the HTLV-1 Proviral Load (PVL) Only in Live Cells: PMA-HTLV-1 Viability PCR In the PVL measurement method based on the usual TaqMan method (Nagai M. J Neurovirol. 1998 December; 4(6):586-93), real-time PCR is performed with DNA purified using a DNA extraction kit from PBMCs containing live cells and dead cells as a template, target gene pX, a TaqMan probe against the internal control gene β-actin, and a primer set. This method is unable to distinguish the live-cell-derived HTLV-1 proviral load (PVL) from the dead-cell-derived HTLV-1 proviral load (PVL) in principle.

In view of the above, a method for measuring PVL only in live cells would make it possible to examine effects of anti-HTLV-1 candidate drugs by comparing PVL levels in live cells in the presence or absence of treatment with anti-HTLV-1 candidate drugs. In a method in which dead cells are removed by a column filled with beads conjugated with Annexin V (i.e., an anticoagulant protein capable of binding to phosphatidyl serine as a membrane GPI anchor structure and $Ca^{2+}$), such as a dead cell removal kit (Miltenyi Biotec 130-090-101), in order to show a decrease in PVL in live cells, dead cells are individually removed and the amount of harvestable DNA is remarkably reduced, making it very difficult to secure the amount and quality of genomic DNA required for PVL measurement. Accordingly, it is inevitable to treat anti-HTLV-1 candidate drugs at low drug concentrations in this method, which leads to an antinomy that makes it difficult to find a significant difference in examination of the effects of anti-HTLV-1 candidate drugs.

Therefore, PMA-HTLV-1 viability PCR is proposed as a method for distinguishing live-cell-derived DNA from dead-cell-derived DNA at the DNA level but not the cell level during real-time PCR.

(2-1) PMA-HTLV-1 Viability PCR as Extended PMA Viability PCR

A method, which comprises steps of, for example, carrying out PMA treatment, DNA extraction. Ct value measurement, and ΔCt value calculation using a standard obtained using, as a target gene (nucleic acid), the HTLV-1 virus pX region integrated in human genomic DNA by applying PMA viability PCR to cells of humans as mammals but no other microorganisms such as bacteria, a primer set, a TaqMan probe, and a pX standard product dilution series in the manner similar to the conventional method for quantitative determination of HTLV-1 PVL, is herein referred to as "PMA-HTLV-1 viability PCR."

(2-2) PMA-HTLV-1 Viability PCR for Measurement of HTLV-1 Only in Live Cells

PMA-HTLV-1 viability PCR is intended to conduct PMA viability PCR for measurement of HTLV-1 pX. Therefore, plots of the number of amplifications (number of cycles)–the amplification product amount (actual number) and plots of the number of copies upon relative expression of CT-gene (expressed as log) (FIGS. 24 and 25) can be directly used.

It is described later that basic issues on PMA viability PCR are directly applicable to PMA-HTLV-1 viability PCR with the use of PBMCs from HAM patients and the HTLV-1-infected cell line Hut102.

It is understood by reconfirming the basic issues that in the case of DNA from a mixture of live and dead cells, the product amount is constant (the C value is constant) regardless of the ratio of live/dead cells in usual PCR using DNA with PMA treatment (−), while on the other hand, when the proportion of live cells is high, the product amount increases and the PCR curve rises early (the Ct value is small) in PMA viability PCR using DNA with PMA treatment (+), and when the proportion of live cells is low, the PCR curve rises late (the Ct value is large). In other words, there is a negative correlation between the product amount and the Ct value.

The early rise (or large Ct value) in PCR using DNA with PMA treatment (−) regarded as usual PCR is derived from DNA extracted from both live and dead cells. On the other hand, the late rise (delayed Ct or large Ct value) in PCR using DNA with PMA treatment (+) regarded as PMA viability PCR is derived from only live cells. This makes it possible to quantitatively determine HTLV-1 PVL using only live cells.

Similarly, ΔCt is derived only from dead cells. Based on the above, the effects of anti-HTLV-1 drugs can be determined.

(3) Assay of Drugs Cytotoxic to HTLV-1-Infected Cells by PMA-HTLV-1 Viability PCR Next, the case of assaying drugs capable of killing HTLV-1-infected cells as a target (i.e., ABL1 inhibitors such as those used in Example 2) using PMA-HTLV-1 viability PCR is considered.

(3-1) Plots of the Number of Amplifications (Number of Cycles)—the Amplification Product Amount (Actual Number) in Assay of Drugs Cytotoxic to HTLV-1-Infected Cells by PMA-HTLV-1 Viability PCR (3-1-1) Extension of the Ct Value by PMA Treatment ($\Delta Ct_{PMA}$) and Extension of the Ct Value by Drug Treatment ($\Delta Ct_{Drug}$)

When target cells die due to candidate drug treatment (Drug treatment), PCR involving amplification of specific nucleic acids (genes) of PMA-treated target cells is inhibited. Accordingly, the Ct value ($Ct_{D+\ P+}$) becomes greater than that in a case in which candidate drug treatment is absent ($Ct_{D-\ P+}$). The Ct value extended by PMA treatment and the Ct value extended by candidate drug treatment are newly defined as $\Delta Ct_{PMA}$ and $\Delta Ct_{Drug}$, respectively, as follows.

$\Delta Ct_{PMA}$=The $Ct_{D-P-}-Ct_{D-P+}$ (corresponding to the formula of the original paper of Nocker A)

$\Delta Ct_{Drug}=Ct_{D-P+}-Ct_{D+P+}$ $Ct_{D-\ P-}$: The Ct value obtained when using DNA with Drug treatment (−). PMA treatment (−), which reflects the amount of DNA from live and dead cells of a drug-untreated specimen $Ct_{D-\ P+}$: The Ct value obtained when using DNA with Drug treatment (−), PMA treatment (+), which reflects the amount of DNA from live cells of a drug-untreated specimen $Ct_{D+\ P+}$: Ct value obtained when using DNA with Drug treatment (+), PMA treatment (+), which reflects the amount of DNA from live cells of a drug-treated specimen $\Delta Ct_{PMA}$ is an index of the amount of DNA only from live cells subjected to PMA treatment, which reflects the ratio of live cells and dead cells that differs for each cell sample. $\Delta Ct_{Drug}$ reflects a decrease in the amount of DNA only from live cells due to drug treatment. Therefore, these values can be used as indexes for determining the cytotoxic effects of drugs on target cells.

Figure 27:
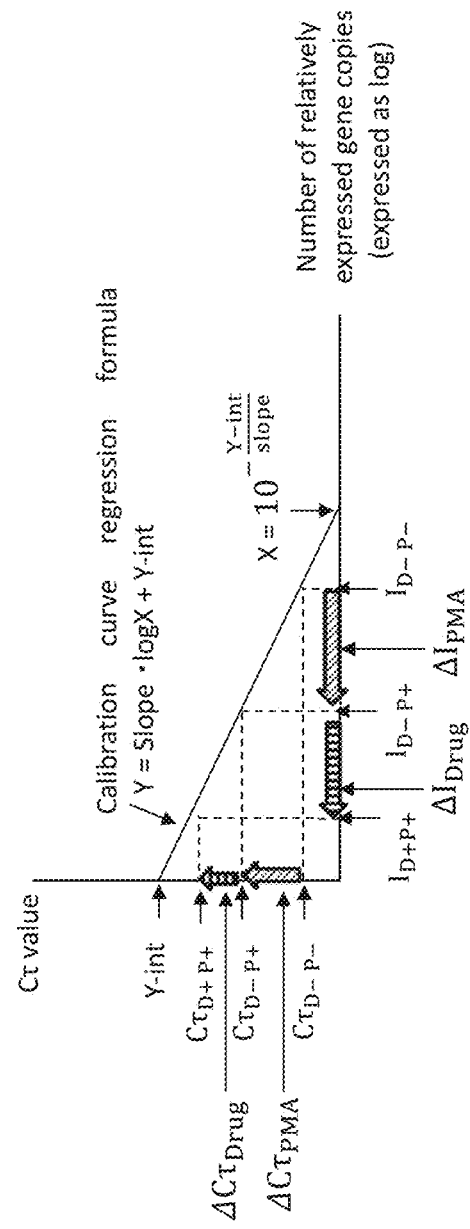
FIG. 27 is a characteristic chart indicating the relationship between Cτ and the number of relatively expressed gene copies (expressed as log) in assay of drugs cytotoxic to HTLV-1-infected cells by PMA-HTLV-1 viability PCR.

(3-2) Plots of Cτ—the Number of Relatively Expressed Gene Copies (Expressed as Log) in Assay of Drugs Cytotoxic to HTLV-1-Infected Cells by PMA-HTLV-1 Viability PCR A standard curve of pX (calibration curve regression formula) was obtained by carrying out the absolute method using a standard sample of a target nucleic acid sequence and the corresponding TAQMAN probe at the same time with PMA viability PCR. By using this standard curve, AC can be plotted on the Y axis (CT) as depicted in FIG. 27.

(3-2-1) Initial Template Reduction Due to PMA Treatment ($\Delta I_{PMA}$), Reduction in the Number of Initial Template Copies Due to Drug Treatment ($\Delta I_{Drug}$)

Similarly, previously defined $\Delta I$ is designated as $\Delta I_{PMA}$ for reduction in the number of initial template copies due to application of PCR based on the plots of Cτ—the number of relatively expressed gene copies, and $\Delta I_{Drug}$ is newly defined to indicate reduction due to candidate drug treatment (Drug treatment) as follows.

$$\Delta I_{PMA} = I_{D-P-} - I_{D-P+}$$

$$\Delta I_{Drug} = I_{D-P+} - I_{D+P+}$$

$I_{D-\ P-}$: The number of initial template copies obtained when using DNA without Drug treatment and without PMA treatment, which corresponds to the number of initial template copies in DNA from live cells and dead cells in a drug-untreated specimen $I_{D-\ P+}$: The number of initial template copies obtained when using DNA without Drug treatment and with PMA treatment, which corresponds to the number of initial template copies in DNA from live cells and dead cells in a drug-untreated specimen $I_{D+\ P+}$: The number of initial template copies obtained when using DNA with Drug treatment and with PMA treatment, which corresponds to the number of initial template copies in DNA from live cells and dead cells in a drug-treated specimen $I_{D-\ P-}$ denotes the number of initial template copies from live cells and dead cells as a whole while $I_{D-\ P+}$ and $I_{D+\ P+}$ each denote the number of initial template copies only from live cells.

$\Delta I_{PMA}$ is an index of the number of initial template copies only from live cells subjected to PMA treatment, which reflects the ratio of live cells and dead cells that differs for each cell sample. $\Delta I_{Drug}$ reflects a decrease in the number of initial template copies only from live cells due to drug treatment. Therefore, these values can be used as indexes for determining the cytotoxic effects of drugs on target cells. It is also possible to calculate $\Delta I_{PMA}$ using the following formula calculated from the standard curve.

[Formula 7]
$$I_{D-P-} = 10^{\frac{C\tau_{D-P-} - Y-int}{slope}},$$
$$I_{D-P+} = 10^{\frac{C\tau_{D-P+} - Y-int}{slope}},$$
$$I_{D+P+} = 10^{\frac{C\tau_{D+P+} - Y-int}{slope}}$$

(3-2-2) the Target Gene Decrease Rate in Live Cells (%) and the Target Gene Survival Rate in Live Cells (%)

In assay of drugs cytotoxic to HTLV-1-infected cells by PMA-HTLV-1 viability PCR, the rate of decrease in the number of target nucleic acid (i.e., the HTLV-1 pX gene) copies (i.e., viral load) in live cells (%) due to candidate drug treatment (Drug treatment) can be calculated by defining the target gene decrease rate in live cells (%) as the proportion with respect to the number of initial template copies only from originally existing live cells. The rate is an index of an effect of reducing the amount of target nucleic acids (i.e., HTLV-1 viral load) by a drug to be assayed, which allows determination of the effect.

[Formula 8]
$$\text{Target gene decrease rate in live cells (\%)} = \frac{\Delta I_{drug}}{I_{D-P+}} \times 100$$
$$= \frac{I_{D-P+} - I_{D+P+}}{I_{D-P+}} \times 100$$
$$= \left(1 - 10^{\frac{C\tau_{D+P+} - C\tau_{D-P+}}{slope}}\right) \times 100$$
$$= \left(1 - 10^{\frac{-\Delta C\tau_{Drug}}{slope}}\right) \times 100$$

As is understood from the above formula, a value obtained by 100—the target gene survival rate in live cells (%) corresponds to the target gene survival rate in live cells.

Example 3

In Example 1, the result that ABL1 inhibitors (imatinib and nilotinib) killed HAM-derived CD4+ T cells in a specific manner is described. In this Example, it was verified whether the ABL1 inhibitors (imatinib and nilotinib) also have an effect of killing asymptomatic carrier (AC)-derived CD4+ T cells in a specific manner.

(3-1) Protocol

In this Example, $5 \times 10^6$ PBMCs frozen and preserved in liquid nitrogen from asymptomatic HTLV-1 carriers (ACs) and negative controls (NCs) (4 cases each) were prepared as specimens. In addition, according to the same method described in [Cell preparation] in Example 1, cells were treated, and drug treatment was carried out according to the same method described in [Drug treatment] in Example 1. Note that in this Example, a drug-untreated well suspension, a 5 μM imatinib-treated well suspension, and a 5 μM nilotinib-treated well suspension of AC specimen #1-derived CD4+ T cells were added in a volume of 25 μL to triplicate wells of the 1st to 3rd columns of column A, the 4th to 6th columns of row A, and the 7th to 9th columns of row A, respectively. Similarly, AC specimen #2-derived CD4+ T cells were added to the 1st to 9th columns of row B, AC specimen #3-derived CD4+ T cells were added to the 1st to 9th columns of row C, and AC specimen #4-derived CD4+ T cells were added to the 1st to 9th columns of row D. In addition, similarly, NC specimen #1-derived CD4+ T cells were added to the 1st to 9th columns of row E, NC specimen #2-derived CD4+ T cells were added to the 1st to 9th columns of row F, NC specimen #3-derived CD4+ T cells were added to the 1st to 9th columns of row G, and NC-derived #4-derived CD4+ T cells were added to the 1st to 9th columns of row H.

Another set of each CD4+ T cell suspensions was added to the 11th to 19th columns of the corresponding row, provided that wells of the 10th column were used as blank wells. Then, 2.5 μL of a 300 μM cytotoxin (digitonin) solution was added to each well in the region of the latter specimens for fluorescence intensity measurement of dead cells, and 2.5 μL of PBS (−) was added to wells in the live cell region of the former specimens to achieve volume equivalence.

Further, also for non-CD4-PBMC cells, a different Nunc 384-well clear polystyrene plate with non-treated surface was prepared, cell suspensions from AC specimens #1 to #4 and NC specimens #1 to #4 were added to the 1st to 16th columns of rows D to F, and a digitonin solution and PBS (−) were added as described above. In the 1st to 12th columns of row G, 25 µl of PBS was added as a no-cell control.

Subsequently, as in the case of Example 1, fluorometry was performed by CellTiter-Fluor Reagent and TECAN Infinite 200M (Tecan Japan Co., Ltd.) (Ex400/Em 505 nm). For the obtained fluorescence intensity, the cell concentration (cells/mL) was calculated by substituting the relative live cell signal (RLU) into the calibration curve regression formula as in the case of Example 1.

(3-2) Results

The relative concentrations (%) in 5 µM imatinib-treated wells and 5 µM nilotinib-treated wells were calculated with respect to the cell concentration of drug-untreated wells which was set to 100. Table 4 lists the results. Here, the values listed in Table 4 each indicate the relative percent (%) of the live cell concentration (cells/mL) with respect to the live cell concentration in drug-untreated wells (relative percent (%)±standard error).

TABLE 4

| Cell type and Specimen origin | | No drug treatment | Imatinib 5 µM 24 h | Nilotinib 5 µM 24 h |
|---|---|---|---|---|
| CD4+ T cells | AC | 100 | 35.47 ± 6.77 | 34.26 ± 5.72 |
| | NC | 100 | 77.99 ± 11.91 | 56.66 ± 19.30 |
| Non-CD4-PBMC | AC | 100 | 85.16 ± 22.26 | 76.78 ± 41.21 |
| | NC | 100 | 109.64 ± 21.88 | 79.78 ± 16.96 |

Figure 28:
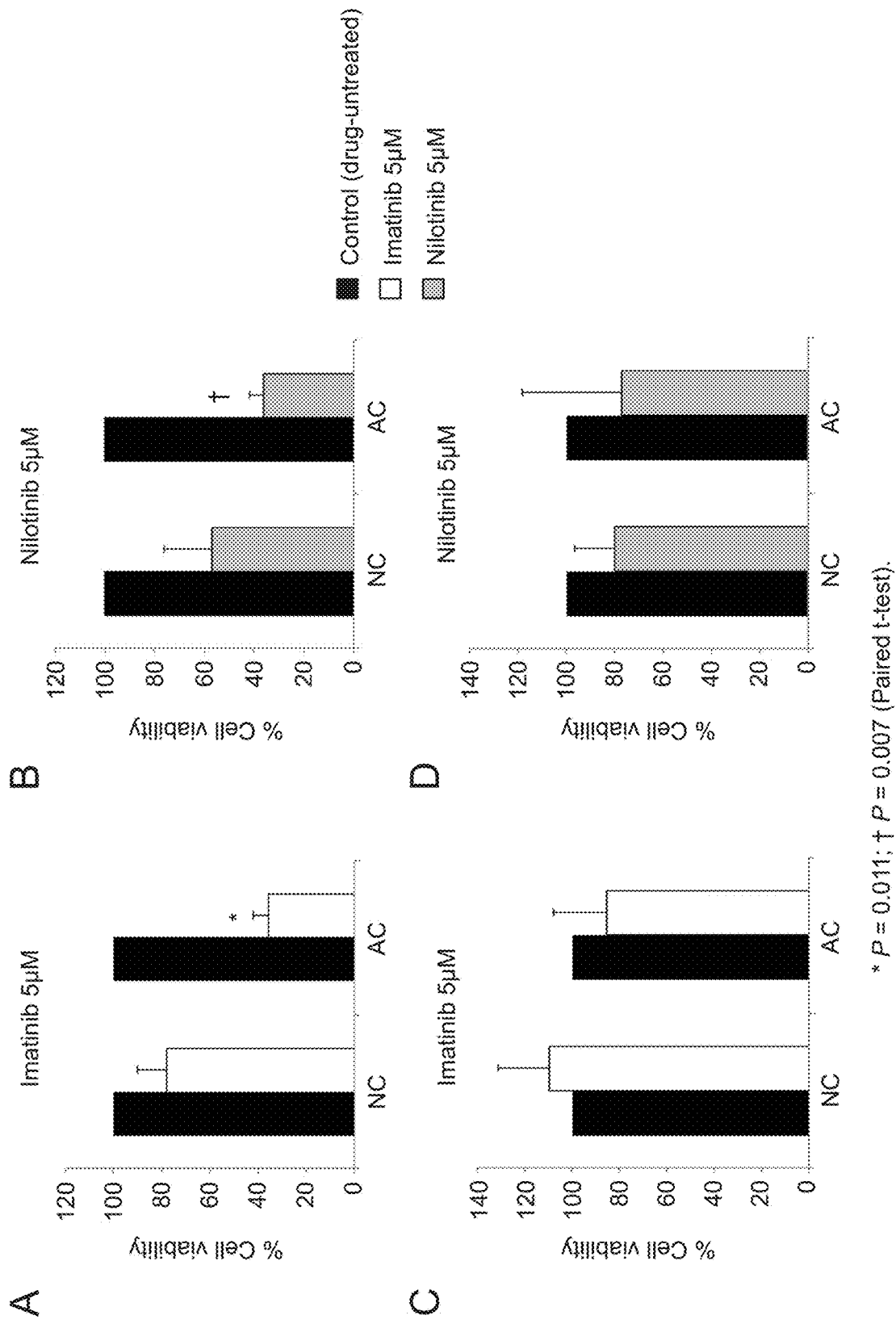
FIG. 28 depicts characteristic charts indicating the effects of ABL1 inhibitors (imatinib and nilotinib) on NC- and AC-derived CD4+ T cells. In the figure, charts A and B indicate the live cell ratio 24 hours after ABL1 inhibitor treatment for CD4+ T cells, and charts C and D indicate the same for non-CD4-PBMC.

FIG. 28 depicts a graph of the results in Table 4 and statistical analysis results. In FIGS. 28, A and B correspond to the results for CD4+ T cells, and C and D correspond to the results for non-CD4-PBMC cells. In FIGS. 28, A and C correspond to the results of 5 µM imatinib treatment, and B and D correspond to the results of 5 JAM nilotinib treatment. In A to D of FIG. 28, the results for NC are depicted on the left side, and the results for AC are depicted on the right side. In addition, in A to D, each black bar represents the drug-untreated cell concentration (cells/mL) set to 100%, each white bar represents the relative cell concentration upon 5 µM imatinib treatment (% cell viability), and each grey bar represents the relative cell concentration upon 5 µM nilotinib treatment (% cell viability).

(3-3) Discussion

As a result of statistical analysis by the relevant t-test, it was found that the cell concentration of AC specimen-derived CD4+ T cells is significantly decreased as compared with NC when the cells are subjected to 5 µM imatinib treatment and 5 µM nilotinib treatment (P=0.011 and P=0.007, respectively). Such effect was not observed for non-CD4-PBMC cells, suggesting that it is an effect of cell death induction by ABL1 inhibitors specific to HTLV-1-infected cells.

As described in this Example and Example 1, it was discovered that ABL1 inhibitors have an effect of preferentially inducing cell death of HAM-derived CD4+ T cells and AC-derived CD4+ T cells, that is to say, HTLV-1-infected CD4+ T cells. In particular, in this Example, it was discovered for the first time in the world that ABL1 inhibitors have an effect of preferentially inducing cell death of asymptomatic carrier (AC)-derived CD4+ T cells as well.

Example 4

In Example 2, it was demonstrated that ABL1 inhibitors (imatinib and nilotinib) have an effect of reducing the proviral load in live cells of HAM-derived CD4+ T cells by applying the method for quantitatively determining the HTLV-1 proviral load only in live cells except dead cells. In this Example, it was verified whether the ABL1 inhibitors have a similar effect of reducing the proviral load in asymptomatic carrier (AC)-derived CD4+ T cells as well.

(4-1) Protocol (4-1-1) Subjects/Cells

PBMCs (1×10$^7$ cells) from 14 AC-derived cases frozen and preserved in liquid nitrogen were used.

(4-1-2) Harvesting at T=0 h (ABL1 Inhibitor-Untreated Specimens)

Specimens frozen and preserved in liquid nitrogen were thawed in a water bath at 37° C. and washed twice with approximately 10 mL of PBS at 300×g during centrifugation for 10 minutes, and resuspended in 1 mL of PBS. The cell concentration was counted by the trypan blue exclusion method. Thereafter, each specimen was divided into two groups such that each group includes approximately 100,000 PBMCs. One of the groups was not subjected to PMA treatment, and the other group was subjected to PMA treatment. The sample groups were named "Sample No-Drug-P−" and "Sample No-Drug-P+," respectively.

A PMA stock solution was added to the sample named "Sample No-Drug-P+" to yield a final concentration of 50 µM in the manner described in Example 2, occasionally shaken under light protection at room temperature for 5 minutes for PMA treatment, and treated with a photo-crosslinker under a halogen lamp for crosslinking during air-cooling for 5 minutes. Genomic DNA was extracted from both samples including the former sample which was not subjected to PMA treatment using DNeazy Blood & Tissue Kits (Cat No 69504, QIAGEN).

(4-1-3) Drug Treatment

RPMI1640 (supplemented with 10% fetal bovine serum, 1% penicillin, and streptomycin) in a volume of 7 mL+α was added to the cell suspension remaining after preparing the two samples in (4-1-2), followed by vortexing. Thereafter, approximately 2 mL of the mixture was dispensed into wells of a 6-well flat bottom polystyrene plate, and imatinib and nilotinib were separately added to achieve imatinib concentrations of 600 nM (IC50) and 5 µM (Cmax) and nilotinib concentrations of 30 nM (IC50) and 3 µM (Cmax), which were equivalent to the concentrations in Example 1. After mixing with a shaker for a short period of time, the cells were cultured in a 5% $CO_2$ incubator.

(4-1-4) Harvesting and PMA Treatment at T=6 h, DNA Extraction

After T=6 h, each specimen was subjected to PMA treatment and crosslinking, and then, genomic DNA was extracted therefrom according to the method described in Example 2.

(4-1-5) Harvesting and PMA Treatment at T=12 h, DNA Extraction

PMA treatment and DNA extraction were carried out according to the method described in Example 2. Accordingly, 10 samples of genomic DNA from each AC sample to be tested, that is to say, 140 samples from 14 specimens, were prepared.

(4-1-6) DNA Concentration Measurement, Working Solution Preparation, Real-Time PCR, and Method for Calculating PMA-HTLV-1 Viability PCR Indexes In this Example, the methods described in Example 2 were used for DNA concentration measurement, working solution preparation, real-time PCR, and the method for calculating PMA-HTLV-1 viability PCR indexes.

(4-1-7) Test

The calculation results were summarized by drugs and concentrations and the above indexes were tested by the t-test (Paired t-test) with a correspondence between concentrations in a time series (T=0 h, 6 h, and 12 h), concentrations by drugs, or drugs by concentrations (IC50 and Cmax). All samples were examined at N=14.

(4-2) Assay Results

Table 5 summarizes the results of assay of ABL1 inhibitors by PMA-HTLV-1 viability PCR obtained by calculating the pX decrease rate in live cells (%) in ABL1 inhibitor treatment.

TABLE 5

| | Drug treatment | | | | | | | | | | | |
|---|---|---|---|---|---|---|---|---|---|---|---|---|
| | Imatinib 600 nM | | | Imatinib 5 μM | | | Nilotinib 30 nM | | | Nilotinib 3 μM | | |
| | Harvesting time | | | | | | | | | | | |
| | 0 h | 6 h | 12 h | 0 h | 6 h | 12 h | 0 h | 6 h | 12 h | 0 h | 6 h | 12 h |
| $\Delta C\tau_{Drug}$ | | | | | | | | | | | | |
| Mean | 0 | −0.28 | −0.98 | 0 | −1.45 | −1.25 | 0 | −1.26 | −1.56 | 0 | −1.05 | −1.36 |
| Standard deviation | 0 | 0.70 | 0.90 | 0 | 1.03 | 1.38 | 0 | 1.02 | 1.48 | 0 | 0.72 | 1.36 |
| Standard error | 0 | 0.19 | 0.24 | 0 | 0.28 | 0.37 | 0 | 0.27 | 0.40 | 0 | 0.19 | 0.36 |
| pX decrease rate in live cells (%) | | | | | | | | | | | | |
| Mean | 0 | 23.83 | 45.46 | 0 | 51.65 | 58.25 | 0 | 53.23 | 71.38 | 0 | 50.50 | 58.56 |
| Standard deviation | 0 | 17.23 | 20.22 | 0 | 21.69 | 27.49 | 0 | 21.65 | 17.74 | 0 | 13.98 | 25.26 |
| Standard error | 0 | 4.97 | 6.10 | 0 | 5.80 | 8.69 | 0 | 6.25 | 5.61 | 0 | 4.04 | 7.61 |

As shown in Table 5, although the results were slightly inferior to those in the case of HAM-derived CD4+ T cells—PBMC described in Example 2, it was demonstrated that both imatinib and nilotinib had an effect of significantly reducing the number of virus copies in live cells upon 12-h treatment at the IC50 concentration by approximately 45% and 71%, respectively, also in the case of AC-derived CD4+ T cells—PBMC, compared to the results obtained without treatment.

(4-3) Discussion

Since the examination at $\Delta C\tau_{Drug}$ and the examination based on the pX decrease rate in live cells are equivalent, for the sake of simplicity, only the pX decrease rate in live cells was employed for discussion. For statistical examination, the paired t-test was used for time-series comparison, the Mann-Whitney U test was used for comparison between concentrations and drugs, and significance was confirmed at †: P<0.05, *: P<0.01.

Figure 29:
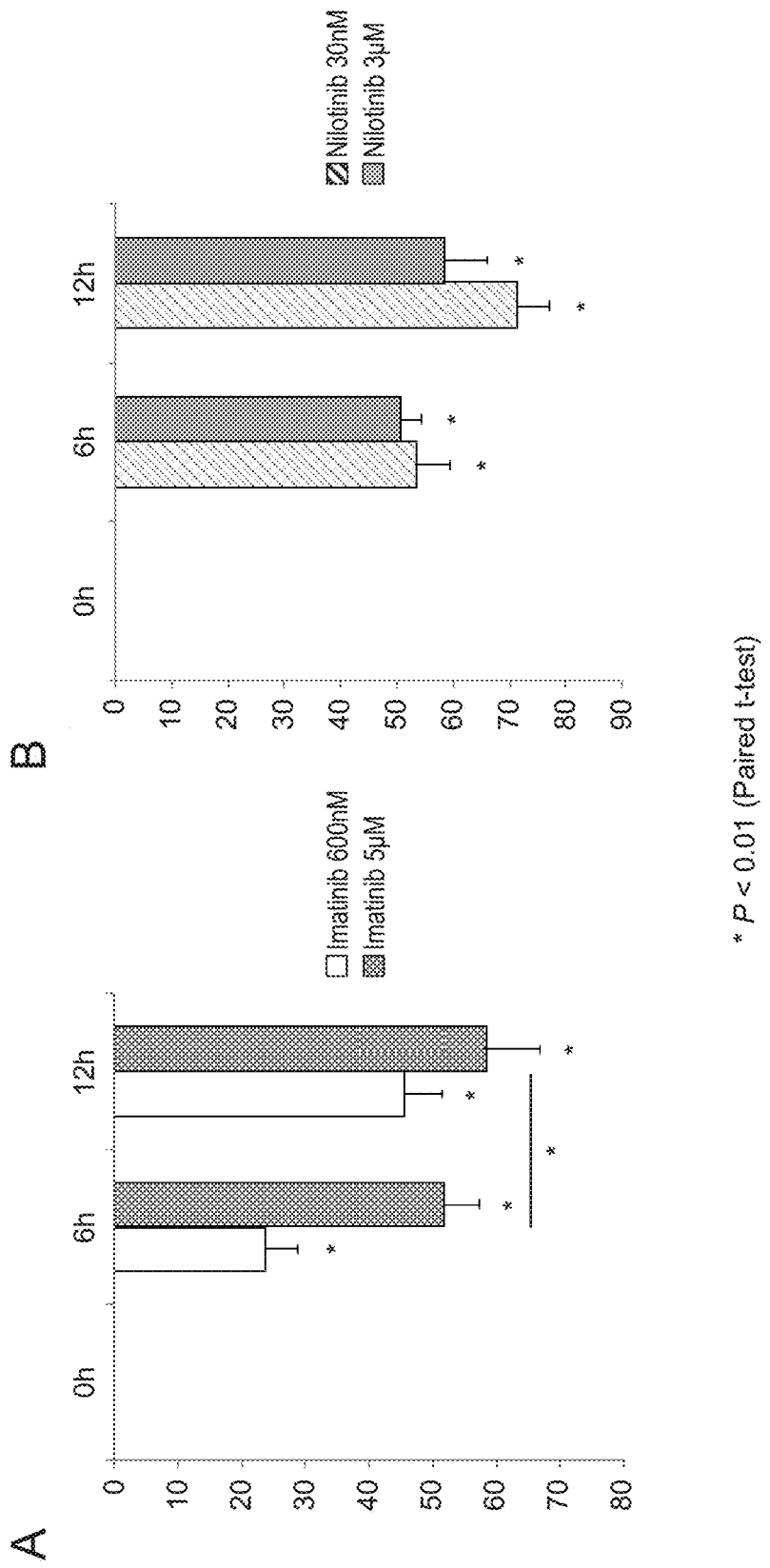
FIG. 29 depicts characteristic charts indicating the relationship between the pX decrease rate in live cells of AC-derived CD4+ T cells and ABL1 inhibitor treatment time. In the figure, the asterisk on each bar indicates a significant difference between T=0 h and T=6 h or T=12 h, and the crossbar above bars indicates a significant difference between the bars below both ends of the crossbar.

(4-3-1) Time-Series Examination (FIG. 29)

FIG. 29 depicts the results. In FIGS. 29, A and B correspond to the results of examination of time-dependent changes in imatinib (600 nM, 5 μM) and nilotinib (30 nM, 3 μM), respectively. As depicted in FIG. 29, there was a significant difference between T=0 h and T=6 h or 12 h with a significance level of less than 1% for both imatinib and nilotinib. There was a significant difference also between 6 h and 12 h with a significance level of less than 1% for 600 nM imatinib (IC50). This is probably because imatinib exhibited a relatively low level of the effect of reducing viruses in live cells at 6 h. However, it is necessary to further analyze whether or not this phenomenon is specific to AC-derived specimens. The effect was sufficiently exhibited at 12 h even in AC-derived specimens.

Figure 30:
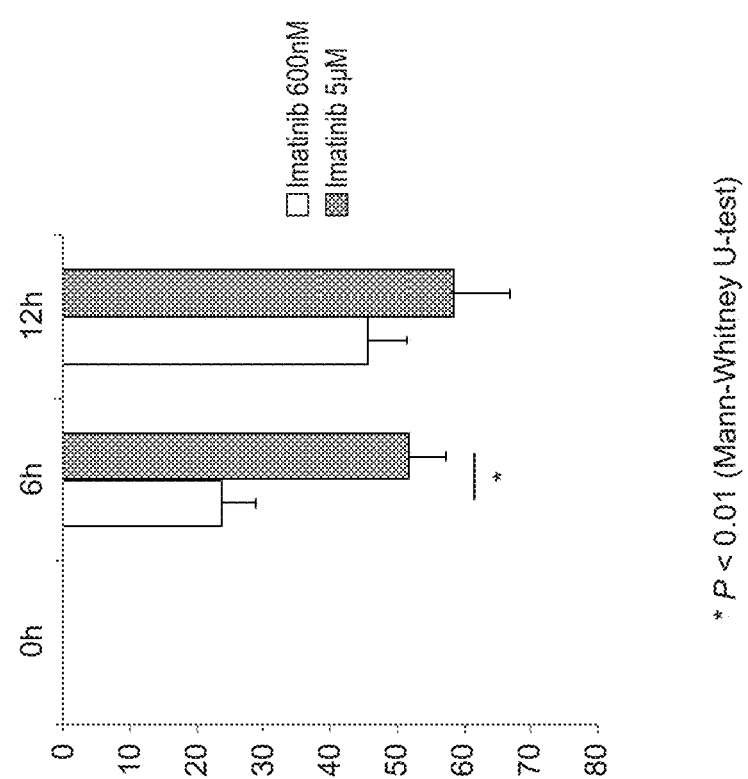
FIG. 30 is a characteristic chart indicating the relationship between the pX decrease rate in live cells of AC-derived CD4+ T cells and the imatinib concentration. In the figure, the crossbar above bars indicates a significant difference between the bars below both ends of the crossbar.

(4-3-2) Examination Between Concentrations (FIG. 30)

It was examined whether there is a difference in the effect depending on concentrations of the same drug at the same time point. FIG. 30 depicts the results. FIG. 30 depicts the results obtained when imatinib was used at 600 nM and 5 μM. As depicted in FIG. 30, there was a significant difference between 600 nM imatinib and 5 μM imatinib at 6 h with a significance level of less than 1%. The rate of virus reduction in live cells in a case in which imatinib was used at 5 μM was higher than that in a case in which imatinib was used at 600 nM. Meanwhile, as depicted in FIG. 30, there was a significant difference at 12 h. Although data are not shown, there was no difference between nilotinib concentrations at 6 h and 12 h.

Figure 31:
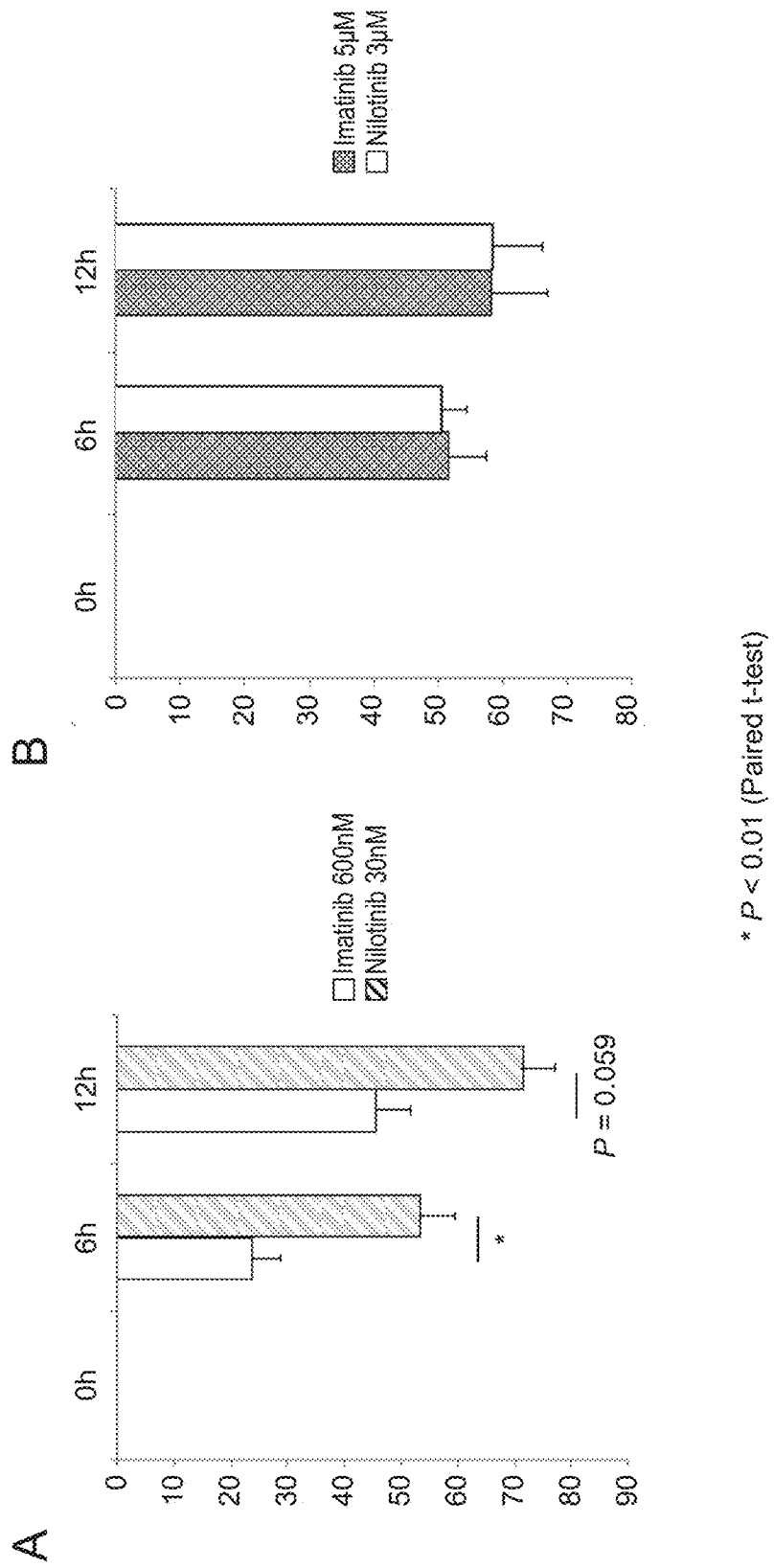
FIG. 31 is a characteristic chart indicating the results obtained by comparing the pX decrease rate in live cells of AC-derived CD4+ T cells between drugs. In the figure, chart A depicts the results of examination of ABL1 inhibitors at their IC50 concentrations, and chart B depicts the results of examination at the Cmax concentrations in the package inserts. In the figure, the crossbar above bars indicates a significant difference between the bars below both ends of the crossbar.

(4-3-3) Examination of Differences Between Drugs (FIG. 31)

FIG. 31 depicts the results. In FIG. 31, chart A corresponds to the results of comparing imatinib (600 nM) and nilotinib (30 nM) at the IC50 concentration, and chart B corresponds to the results of comparing imatinib (5 μM) and nilotinib (3 μM) at the Cmax concentration. As depicted in FIG. 31, there was a significant difference between 600 nM imatinib and 30 nM nilotinib at 6 h with a significance level of less than 1%. In addition, the P value was 0.059 at a time point of 12 h. Thus, at any time point, when nilotinib having higher ABL specificity was used, the rate of virus reduction in live cells was higher as compared with imatinib. This tendency was similar to the tendency observed when HAM-derived CD4+ T cells were used. There was no significant difference between Cmax concentrations thereof as depicted in chart B.

Figure 32:
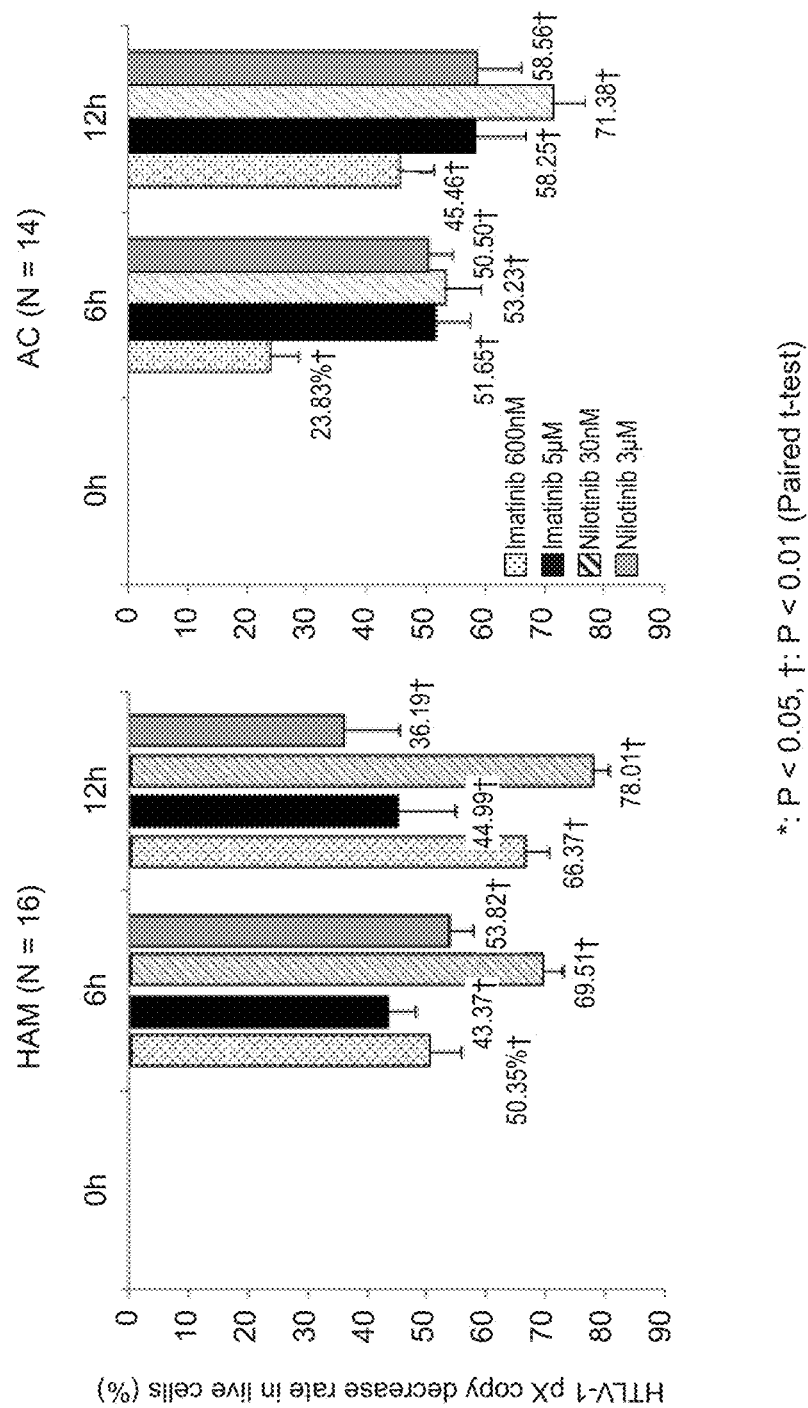
FIG. 32 depicts characteristic charts indicating the results obtained by comparing the effects of the pX decrease rate in live cells between HAM-derived CD4+ T cells and AC-derived CD4+ T cells.

(4-3-4) Comparison of the Effects on HAM-Derived CD4+ T Cells and the Effects on AC-Derived CD4+ T Cells (FIG. 32)

FIG. 32 depicts the results of comparing the results of assay of ABL1 inhibitors by PMA-HTLV-1 viability PCR for HAM-derived CD4+ T cells—PBMC performed in Example 2 and the results of the same assay of AC-derived CD4+ T cells—PBMC performed in this Example. Bars in each graph of FIG. 32 represent the results of imatinib 600 nM, the results of imatinib 5 μM, the results of nilotinib 30 nM, and the results of nilotinib 3 μM in that order from left at 6 h and 12 h.

As depicted in FIG. 32, the rate of decrease in the number of HTLV-1 pX copies in live cells with respect to HAM-derived CD4+ T cells tended to be greater than that with respect to AC-derived CD4+ T cells for the same drug at the same time point and the same concentration. Since the drugs are therapeutic agents based on hyperexpression of ABL1 in the pathogenic mechanism of HAM, the results are presumed to be related to the facts that overexpression is not observed in AC at a level as high as that in HAM and that the decrease rate in AC is lower than that in HAM.

However, a significant decrease at, for example, 6 h and 12 h was continuously observed until 12 h later, there was a significant difference between 12 h and no treatment (T=0 h) while there was no significant difference between 6 h and 12 h for AC. However, the decreasing trend was continuously observed, and the decrease rate reached 71.38% at a maximum for 30 nM nilotinib, which is comparable to that for HAM.

As described above, by considering the results in this Example together with the results in Example 3, it was demonstrated that ABL1 inhibitors such as imatinib and nilotinib have the effect of decreasing the number of HTLV-1 virus copies in live cells of AC-derived CD4+ T cells.

Example 5

[Example of Administration in Humans]

Compared with adult T cell leukemia (ATL)-like animal tumor models, favorable HTLV-1 infected animal models have not been established so far. HAM animal models are in a further difficult situation. It is therefore difficult to verify the HAM improvement effect and the antiviral effect by ABL1 inhibitors in the in vivo system.

Meanwhile, ABL1 inhibitors are drugs which have been established for clinical application in the chronic phase of chronic myelogenous leukemia (CML). Currently, ABL1 inhibitors are pharmaceutical products covered by the health insurance for the clinical application in Japan. CML is a relatively rare disease with a prevalence of 1 per a population of 100,000. Considering the fact that the anti-HTLV-1 antibody-positive rate is 0.1% in Japan, there should be about 10 antibody-positive CML cases on an annual basis.

Therefore, cases who were human CVL patients found to be anti-HTLV-1 antibody-positive and underwent PVL measurement before and after administration of ABL1 inhibitors were searched for, and it was examined whether there was a decrease in PVL after administration of ABL1 inhibitors. As a result, one CML patient was found to be anti-HTLV-1 antibody-positive. This patient developed HAM at 52 years old and was walking with a stick. The patient was not receiving treatment for HAM with steroids, IFN-α, or the like. Eight years later, the patient further developed CML at 60 years old. At such time, a confirmed diagnosis of CML was given because the leukocyte count increased to as high as 27,430/μL, the NAP score was low, and the patient was Philadelphia chromosome-positive. The patient started to orally take imatinib at 400 mg/day, and the dose was reduced to 300 mg/day one month later because of leukopenia. The patient are currently continuing to orally take the drug (as of July 2017). Accordingly, the patient is in a state of molecular genetic remission of CML.

At an imatinib dose of 400 mg/day, the degree of motor function disorder decreased from 5 to 4, and even after the dose was reduced to 300 mg/day, the degree was maintained at 5 and no further exacerbation was observed. In this case, the peripheral blood PVL was 2844 copies before drug administration, it decreased to 1138 copies after 5 months of drug administration, and PVL was confirmed to have obviously decreased to 448 copies/$10^4$ PBMCs 1 year and 5 months after drug administration.

In this example, clinical application examples of administration of ABL1 inhibitors for HTLV-1 were successfully demonstrated in anti-HTLV-1 antibody-positive CML patients. It was possible to demonstrate the obvious PVL lowering effect considered as the effect of ABL1 inhibitors in actual clinical practice. In addition, severe side effects caused by ABL1 inhibitors and unexpected neurological exacerbation did not appear, and therefore, oral administration could be continued, which were important findings.

As described in this Example, the therapeutic effects of ABL1 inhibitors on HTLV-1 in clinical practice were suggested by selecting the anti-HTLV-1 antibody-positive CML patient as a clinical application example of ABL1 inhibitors, instead of HTLV-1-infected animal models, which are currently difficult to use.

All publications, patents and patent applications cited in the present description are incorporated herein by reference in their entirety.

The invention claimed is:

1. A method for treating HTLV-1-associated myelopathy/tropical spastic paraparesis (HAM/TSP) in a subject in need thereof, comprising administering to the subject an effective dose of a substance selected from the group consisting of imatinib, nilotinib, and dasatinib.

2. A method for reducing a HTLV load in a subject in need thereof, comprising administering to the subject an effective dose of a substance selected from the group consisting of imatinib, nilotinib, and dasatinib as an active ingredient.

* * * * *

UNITED STATES PATENT AND TRADEMARK OFFICE
CERTIFICATE OF CORRECTION

PATENT NO. : 10,772,887 B2  Page 1 of 1
APPLICATION NO. : 16/322356
DATED : September 15, 2020
INVENTOR(S) : Daisuke Kodama and Shuji Izumo It is certified that error appears in the above-identified patent and that said Letters Patent is hereby corrected as shown below:

On the Title Page

Item (72) Inventors: Column 1, Line 1:
Daisuke Kodama, "Kogoshima (JP)" should be --Kagoshima (JP)--.

Signed and Sealed this
Nineteenth Day of January, 2021

Andrei Iancu
*Director of the United States Patent and Trademark Office*